(12) United States Patent
Isono et al.

(10) Patent No.: US 7,887,990 B2
(45) Date of Patent: Feb. 15, 2011

(54) FLUORINE-CONTAINING COMPOUND, FLUORINE-CONTAINING POLYMER, POSTIVE-TYPE RESIST COMPOSITION, AND PATTERNING PROCESS USING SAME

(75) Inventors: Yoshimi Isono, Kawagoe (JP); Jonathan Joachim Jodry, Kawagoe (JP); Satoru Narizuka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 339 days.

(21) Appl. No.: 12/137,145

(22) Filed: Jun. 11, 2008

(65) Prior Publication Data
US 2008/0311507 A1 Dec. 18, 2008

(30) Foreign Application Priority Data
Jun. 12, 2007 (JP) ............................. 2007-155165

(51) Int. Cl.
G03F 7/004 (2006.01)
G03F 7/30 (2006.01)
C08F 20/22 (2006.01)

(52) U.S. Cl. .................... 430/270.1; 430/326; 430/907; 430/910; 526/292.1

(58) Field of Classification Search .............. 430/270.1, 430/326, 907, 910; 526/292.1
See application file for complete search history.

(56) References Cited

U.S. PATENT DOCUMENTS

| 5,968,713 | A | 10/1999 | Nozaki et al. | |
| 6,013,416 | A | 1/2000 | Nozaki et al. | |
| 6,200,725 | B1 | 3/2001 | Takechi et al. | |
| 6,329,125 | B2 | 12/2001 | Takechi et al. | |
| 6,800,418 | B2 * | 10/2004 | Yoon et al. | 430/270.1 |
| 2009/0011199 | A1 * | 1/2009 | Isono et al. | 428/195.1 |
| 2009/0061353 | A1 * | 3/2009 | Isono et al. | 430/270.1 |

FOREIGN PATENT DOCUMENTS

| JP | 1-242551 A | 9/1989 |
| JP | 10-161313 A | 6/1998 |
| JP | 2000-89463 A | 3/2000 |
| JP | 2007-86514 A | 4/2007 |

OTHER PUBLICATIONS

E. Ann Hallinan et al., "2,2-Difluoro-3-Hydroxyesters By Reformatskii Reaction" Tetrahedron Letters, vol. 25, No. 22, pp. 2301-2302, 1984.
Korean Office Action dated Nov. 19, 2009.
Akahoshi et al., Synthesis, Structure-Activity Relationships, and Parmacokinetic Profiles of Nonpeptidic Difluoromethylene Ketones as Novel Inhibitors of Human Chymase, J. Med. Chem., 2001, 44, 1297-1304.
Posner et al., Noncalcemic, Antiproliferative, Transcriptionally Active, 24-Fluorinated Hybrid Analogues of the Hormone 1α, 25-Dihydroxyvitamin D₃_ Synthesis and Preliminary Biological Evaluation. J. Med. Chem., 1998, 41, 3008-3014.

* cited by examiner

*Primary Examiner*—John S Chu
(74) *Attorney, Agent, or Firm*—Crowell & Moring LLP

(57) ABSTRACT

Disclosed is a fluorine-containing compound represented by formula (1),

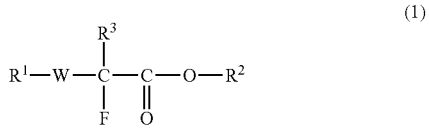

(1)

wherein $R^1$ represents a polymerizable double-bond containing group, $R^2$ represents an acid-labile protecting group, $R^3$ represents a fluorine atom or fluorine-containing alkyl group, and W represents a bivalent linking group. This compound can provide a fluorine-containing polymer compound that has a weight-average molecular weight of 1,000-1,000,000 and contains a repeating unit represented by formula (2),

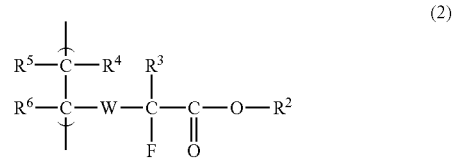

(2)

wherein $R^2$, $R^3$ and W are defined as above, each of $R^4$, $R^5$ and $R^6$ independently represents a hydrogen atom, fluorine atom or monovalent organic group, at least two of $R^4$, $R^5$ and $R^6$ may be combined to form a ring. This polymer compound can provide a resist composition capable of forming a pattern that is transparent to exposure light and superior in rectangularity.

17 Claims, No Drawings

FLUORINE-CONTAINING COMPOUND, FLUORINE-CONTAINING POLYMER, POSTIVE-TYPE RESIST COMPOSITION, AND PATTERNING PROCESS USING SAME

BACKGROUND OF THE INVENTION

The present invention relates to a novel fluorine-containing compound, a fluorine-containing polymer compound derived therefrom, a positive-type resist composition using the polymer compound, and a pattern forming process by the resist composition.

In recent years, throughput of operation data and of two-dimensional and three-dimensional image data has become enormous by the development of digital equipment, such as computer. In order to achieve a rapid processing of such information, there arises a demand for a high-capacity, high-speed memory and a high-performance microprocessor. Furthermore, a demand for processing ability on digital equipment is expected to become increasingly high, due to a further acceleration of broadbandization along with the development of network such as Internet.

To satisfy this demand, various devices, such as semiconductor devices, are required to have a further high-density and a further high integration. In particular, a demand for a photolithography that makes microfabrication possible has become strict year to year. For producing a DRAM having an integration degree of 1G bits or more, it is necessary to have a processing technology of a minimum line width of 0.13 micrometers or less. In response to this, a photolithography using ArF excimer laser (193 nm) is used. Furthermore, the development of a photolithography using $F_2$ excimer laser (157 nm) is in progress for the purpose of forming fine patterns.

In these wavelength regions, it is not possible to use novolac resins and polyvinyl phenol resins, which have conventionally been used for resist compositions, since their light absorptions are too large. Thus, acrylic resins (see Japanese Patent Application Publication 10-161313) and cycloolefinic resins (see Japanese Patent Application Publication 2000-089463) have been examined.

In the case of forming patterns by using a photoresist composition, a tetramethylammonium aqueous solution (TMAH aqueous solution) is favorably used, in place of organic solvent as a developing solution, due to environmental concern. Phenolic hydroxyl group, carboxyl group, and hexafluoroisopropanol group are known as functional groups that are soluble in TMAH aqueous solution, that is, functional groups that make a development by TMAH aqueous solution possible. In the case of using wavelengths of ArF (193 nm) and $F_2$ (157 nm), aromatic ring has intense absorption bands at the both wavelength regions. Therefore, carboxyl group or hexafluoroisopropanol is mainly in examination. In the case of forming particularly fine patterns, resins having a hexafluoroisopropanol group provide resist compositions that are superior in transparency, development property, and adhesion to substrate, thereby providing relatively good patterns. It is, however, known that a special synthesis technique is necessary for forming those resins. On the other hand, resins having a carboxyl group as the functional group swell in TMAH aqueous solution. Therefore, it is difficult to obtain patterns as originally designed (see Japanese Patent Application Publication 2007-086514).

As carboxylic compounds having a fluorine atom at α-position, 2-fluorophenylacetic acid and its ester (see Japanese Patent Application Publication 1-242551) and ethyl 2,2-difluoro-3-hydroxy-3-phenylpropionate (see Tetrahedron Letters, Vol. 25, No. 22, pp 2301-2302, 1984) are known.

SUMMARY OF THE INVENTION

It is an object of the present invention to provide (a) a resist composition capable of forming a pattern that is transparent to exposure light and superior in rectangularity by providing a fluorine-containing polymer compound, which constitutes the resist composition used for forming patterns by using a high-energy ray of 300 nm or shorter or electron beam, with a novel carboxyl-containing structure, and (b) a fluorine-containing compound that is useful for introducing the structure into the fluorine-containing polymer compound.

The present inventors have conducted en eager examination on solubility of a resist film derived from a fluorine-containing polymer compound having a carboxyl group as an acid-decomposing moiety in its repeating unit, in TMAH aqueous solution. With this, we have found that the resist film dissolves at its exposed portion without having swelling at its unexposed portion by introducing a fluorine atom at α-position of the carboxyl group, thereby forming patterns as originally designed. Upon this, we also have found a novel, polymerizable, fluorine-containing compound that is useful for introducing a fluorine atom into α-position of the carboxyl group of the fluorine-containing polymer compound.

Although the fluorine-containing polymer compound, which is an important component of the resist composition of the present invention, does not contain a hetero atom, such as sulfur or phosphorus, in its acid-decomposing moiety, it is possible to increase acidity of the acid-decomposing moiety, thereby easily eliminating the acid-labile protecting group.

According to the present invention, there is provided a fluorine-containing compound represented by formula (1),

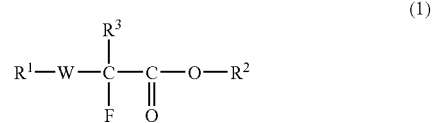

(1)

wherein $R^1$ represents a polymerizable double-bond containing group, $R^2$ represents an acid-labile protecting group, $R^3$ represents a fluorine atom or fluorine-containing alkyl group, and W represents a bivalent linking group.

According to the present invention, there is provided a fluorine-containing polymer compound comprising a repeating unit (a) represented by formula (2),

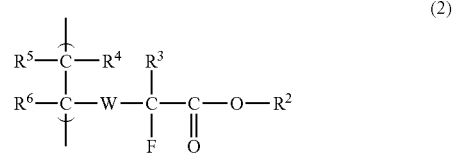

(2)

wherein $R^2$, $R^3$ and W are defined as in formula (1), each of $R^4$, $R^5$ and $R^6$ independently represents a hydrogen atom, fluorine atom or monovalent organic group, and at least two of $R^4$, $R^5$ and $R^6$ may be combined to form a ring, wherein the fluorine-containing polymer compound has a weight-average molecular weight of 1,000 to 1,000,000.

A partial structure R¹—W— in formula (1) may include a group selected from the group consisting of the following groups,

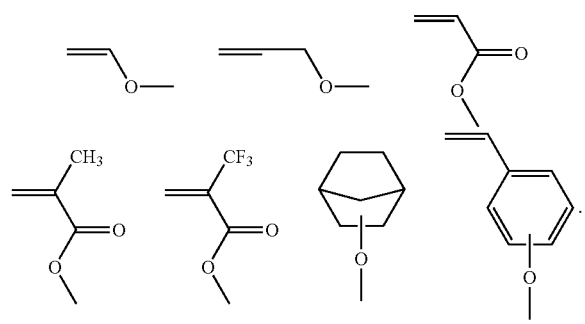

In formulas (1) and (2), W may represent a bivalent linking group selected from the group consisting of a single bond, —(CR⁷R⁸)ₙ— (wherein n represents an integer of 1-10, each of R⁷ and R⁸ independently represents a monovalent organic group, and R⁷ and R⁸ may be combined to form a ring), —O—, —C(=O)—, —C(=O)O—, —O—C(=O)—, a bivalent alicyclic hydrocarbon group, a bivalent aromatic hydrocarbon group, a thioether group, an ester group, an amide group, a sulfonamide group, a urethane group, a urea group, and combinations of these.

The fluorine-containing compound may be selected from the group consisting of the following compounds,

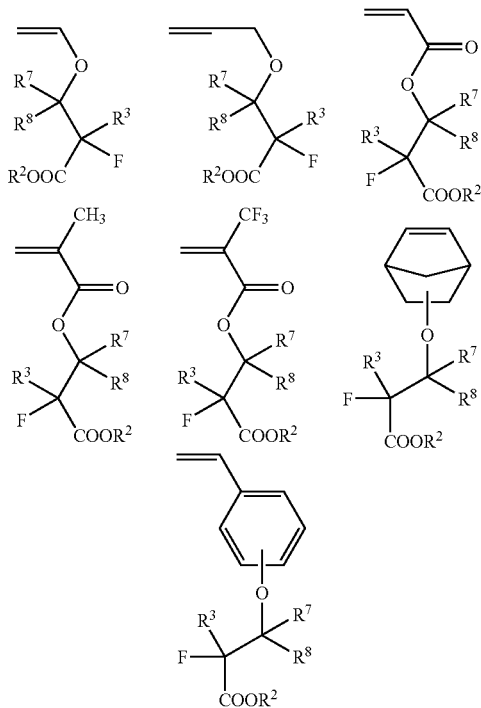

wherein R² is defined as above, R³ represents a fluorine atom or trifluoromethyl group, R⁷ represents a hydrogen atom or a straight-chain, branched or cyclic alkyl or fluoroalkyl group, R⁸ represents a straight-chain, branched or cyclic alkyl or fluoroalkyl group, and R⁷ and R⁸ may be combined to form a ring.

The fluorine-containing polymer compound may include a structure formed by cleavage of a polymerizable double bond of a compound selected from the group consisting of the above seven compounds.

In the above seven formulas, each of R⁷ and R⁸ independently may represent a C₁-C₄ straight-chain or branched alkyl or fluoroalkyl group or a C₃-C₁₀ cyclic alkyl or fluoroalkyl group, or R⁷ and R⁸ may be bonded together to form a C₄-C₈ alicyclic hydrocarbon group.

In the above seven formulas, R⁷ may represent a hydrogen atom or a monovalent organic group selected from the group consisting of methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group, and R⁸ may represent a monovalent organic group selected from the group consisting of methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group. Alternatively, R⁷ and R⁸ may be bonded together to form a cyclopentyl group, cyclohexyl group or cycloheptyl group.

In formulas (1) and (2), R² may be a monovalent organic group selected from the group consisting of R¹¹—O—C(=O)—, R¹¹—O—CHR¹²—, CR¹³R¹⁴R¹⁵—, SiR¹³R¹⁴R¹⁵—, and R¹¹—C(=O)—, where R¹¹ represents an alkyl group, alicyclic hydrocarbon group, or aryl group; R¹² represents a hydrogen atom, alkyl group, alicyclic hydrocarbon group, alkenyl group, aralkyl group, alkoxy group, or aryl group; each of R¹³, R¹⁴ and R¹⁵ independently represents an alkyl group, alicyclic hydrocarbon group, alkenyl group, aralkyl group, or aryl group; and at least two groups of R¹³, R¹⁴ and R¹⁵ may be combined to form a ring.

In formula (1), R² may represent a methoxymethyl or t-butyl group.

A partial structure in formula (2), which is represented by formula (9-1),

(9-1)

may include a structure formed by cleavage of a polymerizable double bond of a group selected from the group consisting of the following groups,

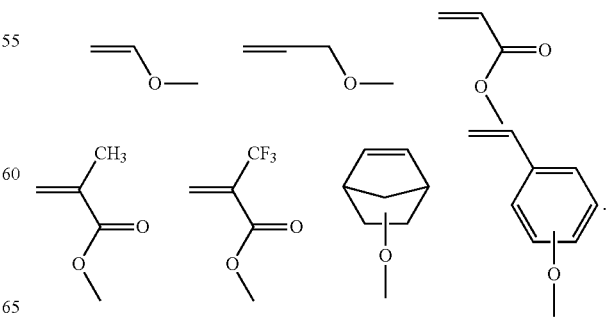

The fluorine-containing polymer compound may include a structure formed by cleavage of a polymerizable double bond of a compound selected from the group consisting of the following compounds,

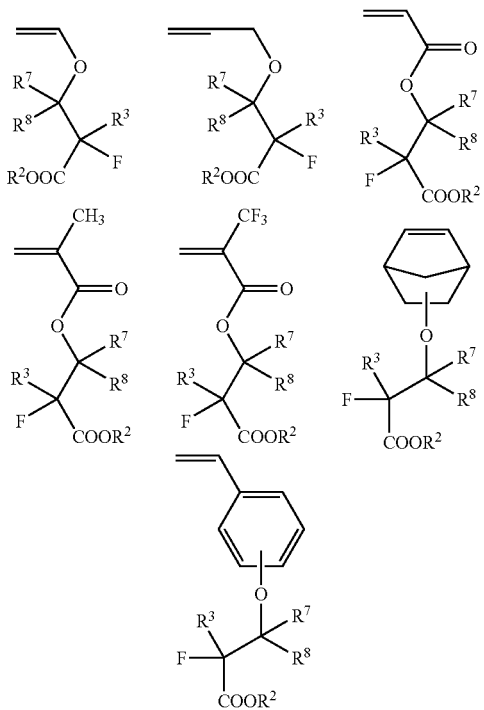

wherein $R^2$ and $R^3$ are defined as in formula (1), and $R^7$ and $R^8$ are defined as above.

The fluorine-containing polymer compound may further include a repeating unit having a side chain with a lactone ring.

The fluorine-containing polymer compound may further include a repeating unit (b) derived from a polymerizable monomer selected from the group consisting of acrylates, fluorine-containing acrylates, methacrylates, fluorine-containing methacrylates, styrene compounds, fluorine-containing styrene compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds, fluorine-containing norbornene compounds, sulfur dioxide, and vinyl silanes.

The fluorine-containing polymer compound may further include a repeating unit (b), and the repeating unit (a) represented by formula (2) and the repeating unit (b) may respectively be in 0.1-99.9 mol % and 99.9-0.1 mol %, based on a total mole number of all repeating units contained in the fluorine-containing polymer compound.

According to the present invention, there is provided a resist composition including the fluorine-containing polymer; an acid generator; and a solvent.

According to the present invention, there is provided a process for forming a pattern, including the steps of:

(a) applying the resist composition on a substrate to form a resist film;

(b) exposing the resist film to a high-energy ray having a wavelength of 300 nm or shorter or electron beam through a photomask;

(c) heating the exposed resist film; and (d) developing the heated resist film.

The process may further include the step of (e) heating the resist film, between the steps (a) and (b).

In step (b), the high-energy ray may be a $F_2$ excimer laser, ArF excimer laser, KrF excimer laser, or soft X-ray.

According to the present invention, there is provided an electronic device including a pattern formed by the process.

DETAILED DESCRIPTION

In the specification and the claims, alkyl group is defined as containing straight-chain, branched and cyclic alkyl groups. Cyclic alkyl group is defined as a part of alicyclic group or alicyclic hydrocarbon group. The term of "lower" as in lower alkyl group and other groups refers to a carbon atom number of 1-4. However, the term of "lower" as to cyclic alkyl group refers to one having a cyclic structure of a carbon atom number of 3-10, and cyclic alkyl group may have a lower alkyl group (e.g., methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group and 3,3,3-trifluoropropyl group) as a substituent. Hereinafter, when a compound having isomers is exemplified, only its typical name and structure may be described for simplification, but it is defined as including all of its isomers.

In the specification, halogen refers to fluorine, chlorine, bromine or iodine.

A resist composition of the present invention provides an outstanding effect. That is, a portion of the resist film exposed to a high-energy ray having a wavelength of 300 nm or shorter or electron beam becomes soluble in a TMAH aqueous solution, and the resulting pattern (unexposed portion) shows a superior rectangularity. In case that the fluorine-containing compound represented by formula (1) contains an acid-labile protecting group (e.g., acetal group) having a chemically amplifying function, the resist composition derived from such fluorine-containing compound shows transparency and a superior rectangularity of the pattern, even if the resist film is exposed to a high-energy ray having a wavelength of 200 nm or shorter or electron beam. Furthermore, a fluorine-containing compound of the present invention has an advantageous effect in which an acid-labile protecting group can easily and efficiently be introduced into a fluorine-containing polymer, which constitutes a resist composition of the present invention.

Thus, a resist composition of the present invention can preferably be used as a positive-type resist composition, particularly as a chemically-amplified resist composition by containing an acid-labile protecting group. A fluorine-containing polymer compound of the present invention can preferably be used for such resist composition. Furthermore, a fluorine-containing compound of the present invention is one suitable for introducing an acid-labile protecting group into the fluorine-containing polymer compound.

In the following, the present invention is exemplarily described in detail by embodiments. The present invention is, however, not limited to the embodiments. A skilled person in the art may suitably conduct a modification, improvement or the like on the following embodiments without deviating from the gist of the present invention, and such modification, improvement or the like is in the scope of the present invention.

The fluorine-containing polymer compound represented by formula (2) of the present invention is one having a polymer skeleton formed by a homopolymerization through cleavage of a polymerizable double bond of the fluorine-containing compound represented by formula (1) or a copolymerization therethrough with another monomer having a polymerizable double bond.

As shown by formula (2), the fluorine-containing polymer compound of the present invention is characterized in that a chain skeleton formed through cleavage of the polymerizable double bond is bonded to a carboxyl group (COOR$^2$) through a bivalent linking group W and that this carboxyl group has an acid-labile protecting group R$^2$ through ester bond and is bonded to the bivalent linking group W through α-position carbon, to which a fluorine atom and a fluorine atom or fluorine-containing alkyl group R$^3$ are bonded.

Fluorine-Containing Polymer Compound

The fluorine-containing polymer represented by formula (2) is a resin of which rate of dissolution increases in alkali developing solution by an action of acid, and which has a group (acid-decomposing group) that is decomposed by an action of acid and becomes alkali-soluble. Of the acid-decomposing group, a leaving moiety is referred to as an acid-labile protecting group.

As stated above, R$^3$ of the fluorine-containing polymer compound is a fluorine atom or fluorine-containing alkyl group. Although this fluorine-containing alkyl group is not particularly limited, it may have a carbon atom number of 1-12, preferably 1-3. Its examples include trifluoromethyl group, pentafluoroethyl group, 2,2,2-trifluoroethyl group, n-heptafluoropropyl group, 2,2,3,3,3-pentafluoropropyl group, 3,3,3-trifluoropropyl group, and hexafluoroisopropyl group. R$^3$ is more preferably a fluorine atom or trifluoromethyl group.

The purpose of introducing an acid-labile protecting group into the fluorine-containing polymer compound, which constitutes a main component of the resist composition, is to exhibit a positive-type photosensitivity by the acid-labile protecting group and to exhibit a solubility of the resist in an alkali aqueous solution after exposure to a high-energy ray (e.g., far-ultraviolet ray, excimer laser, and X-ray) having a wavelength of 300 nm or shorter or electron beam. It is possible to change and adjust polarity of the polymer terminal by changing the type of the acid-labile protecting group or the ratio of the acid-labile protecting group to a stable group (i.e., a group of which terminal is not an acid-labile protecting group defined hereinafter as R$^2$). With this, it is possible to suitably adjust solubility in solvent, coatability onto substrate, surface tension, dispersibility of the acid generator, acid diffusion rate, etc. A fluorine-containing polymer compound of the present invention with a large number of fluorine atoms in the molecule can improve the resist film in transparency. In contrast, one with a cyclic structure can provide the resist film with characteristics such as etching resistance and high glass transition point. Thus, it is possible to use different molecular structures of the polymer compound for different purposes.

Examples of the acid-labile protecting group R$^2$ include R$^{11}$—O—C(=O)—, R$^{11}$—O—CHR$^{12}$—, CR$^{13}$R$^{14}$R$^{15}$—, SiR$^{13}$R$^{14}$R$^{15}$—, and R$^{11}$—C(=O)—. Of these, R$^{11}$—O—C(=O)—, R$^{11}$—O—CHR$^{12}$— and CR$^{13}$R$^{14}$R$^{15}$— function as chemically amplified type. Therefore, these three groups are particularly preferable for producing a resist composition to be used in a pattern forming process in which exposure is conducted by a high-energy ray.

R$^{11}$ represents an alkyl group, alicyclic hydrocarbon group, or aryl group (aromatic hydrocarbon group). R$^{12}$ represents a hydrogen atom, alkyl group, alicyclic hydrocarbon group, alkenyl group, aralkyl group, alkoxy group, or aryl group. Each of R$^{13}$, R$^{14}$ and R$^{15}$ independently represents an alkyl group, alicyclic hydrocarbon group, alkenyl group, aralkyl group, or aryl group. At least two groups of R$^{13}$, R$^{14}$ and R$^{15}$ may be combined to form a ring.

The alkyl group for R$^{11}$ to R$^{15}$ is preferably one having a carbon number of 1-4, such as methyl group, ethyl group, propyl group, isopropyl group, n-butyl group, sec-butyl group, and tert-butyl group. The alicyclic hydrocarbon group therefor may be one having a carbon number of 3-30, such as cyclopropyl group, cyclopentyl group, cyclohexyl group, adamantyl group, norbornyl group, bornyl group, tricyclodecanyl group, dicyclopentenyl group, norbornaneepoxy group, menthyl group, isomenthyl group, neomenthyl group, tetracyclododecanyl group, and steroid residue. The alkenyl group for R$^{12}$ to R$^{15}$ is preferably one having a carbon number of 2-4, such as vinyl group, propenyl group, allyl group, and butenyl group. The aryl group for R$^{11}$ to R$^{15}$ is preferably one having a carbon number of 6-14, such as phenyl group, xylyl group, tolyl group, cumenyl group, naphthyl group, and antracenyl group, and these groups may have substituents. The aralkyl group for R$^{12}$ to R$^{15}$ may be one having a carbon number of 7-20, optionally having a substituent. Examples of the aralkyl group include benzyl group, phenethyl group, and cumyl group.

Examples of optional substituents of the organic groups R$^{11}$ to R$^{15}$ include hydroxyl group, halogen atoms, nitro group, cyano group, the above-exemplified alkyl groups and alicyclic hydrocarbon groups, alkoxy groups (e.g., methoxy group, ethoxy group, hydroxyethoxy group, propoxy group, hydroxypropoxy group, n-butoxy group, isobutoxy group, sec-butoxy group, and tert-butoxy group), alkoxycarbonyl groups (e.g., methoxycarbonyl group and ethoxycarbonyl group), aralkyl groups (e.g., benzyl group, phenethyl group, and cumyl group), acyl groups (e.g., aralkyloxy group, formyl group, acetyl group, butyryl group, benzoyl group, cyanamyl group, and valeryl group), acyloxy groups (e.g., butyloxy group), the above-exemplified alkenyl groups, alkenyloxy groups (e.g., vinyloxy group, propenyloxy group, allyloxy group, and butenyloxy group), the above-exemplified aryl groups, aryloxy groups (e.g., phenoxy group), and aryloxycarbonyl groups (e.g., benzoyloxy group).

Further examples of the optional substituents of R$^{11}$ to R$^{15}$ include lactone groups represented by the following formulas (3-1) and (3-2),

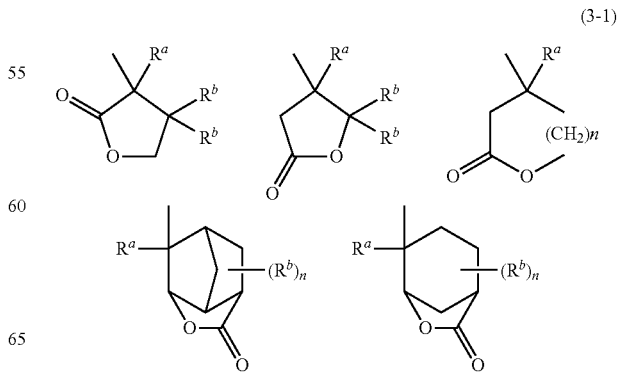

(3-1)

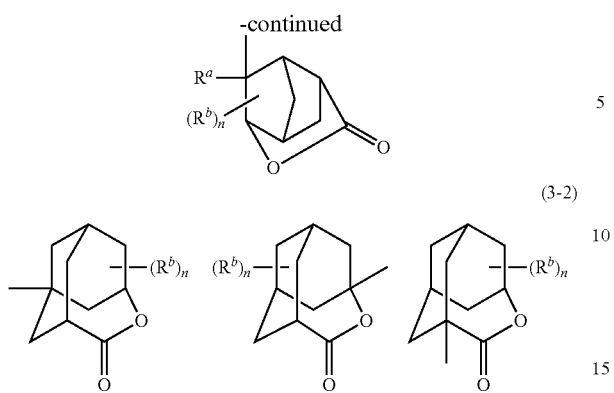

(3-2)

wherein $R^a$ represents a $C_1$-$C_4$ alkyl or perfluoroalkyl group. Each of $R^b$'s independently represents a hydrogen atom, $C_1$-$C_4$ alkyl or perfluoroalkyl group, hydroxy group, carboxyl group, alkyloxycarbonyl group or alkoxy group, and n represent an integer of 1-4.

In the following, specific examples of the above-mentioned acid-labile protecting group $R^2$ are shown.

Examples of the alkoxycarbonyl group $R^{11}$—O—C(=O)— include tert-butoxycarbonyl group, tert-amyloxycarbonyl group, methoxycarbonyl group, ethoxycarbonyl group, i-propoxycarbonyl group, cyclohexyloxycarbonyl group, isobornyloxycarbonyl group, and adamantaneoxycarbonyl group.

Examples of the acetal group $R^{11}$—O—CHR$^{12}$— include methoxymethyl group, ethoxymethyl group, 1-ethoxyethyl group, 1-butoxyethyl, 1-isobutoxyethyl, 1-cyclohexyloxyethyl group, 1-benzyloxyethyl group, 1-phenethyloxypropyl group, 1-ethoxybutyl group, 1-cyclohexyloxyethyl group, 1-ethoxyisobutyl group, 1-methoxyethoxymethyl group, tetrahydropyranyl group and tetrahydrofuranyl group. Further examples include acetal groups obtained by adding vinyl ethers to hydroxy group.

Examples of the tertiary hydrocarbon group $CR^{13}R^{14}R^{15}$— include tert-butyl group, tert-amyl group, 1-dimethylpropyl group, 1-ethyl-1-methylpropyl group, 1,1-dimethylbutyl group, 1-ethyl-1-methylbutyl group, 1,1-diethylpropyl group, 1,1-dimethyl-1-phenylmethyl group, 1-methyl-1-ethyl-1-phenylmethyl group, 1,1-diethyl-1-phenylmethyl group, 1-methylcyclohexyl group, 1-ethylcyclohexyl group, 1-methylcyclopentyl group, 1-ethylcyclopentyl group, 1-isobornyl group, 1-methyladamantyl group, 1-ethyladamantyl group, 1-isopropyladamantyl group, 1-isopropylnorbornyl group, and 1-isopropyl-4-methylcyclohexyl group.

In the following, specific examples of the acid-labile protecting group $R^2$ containing an alicyclic hydrocarbon group are shown.

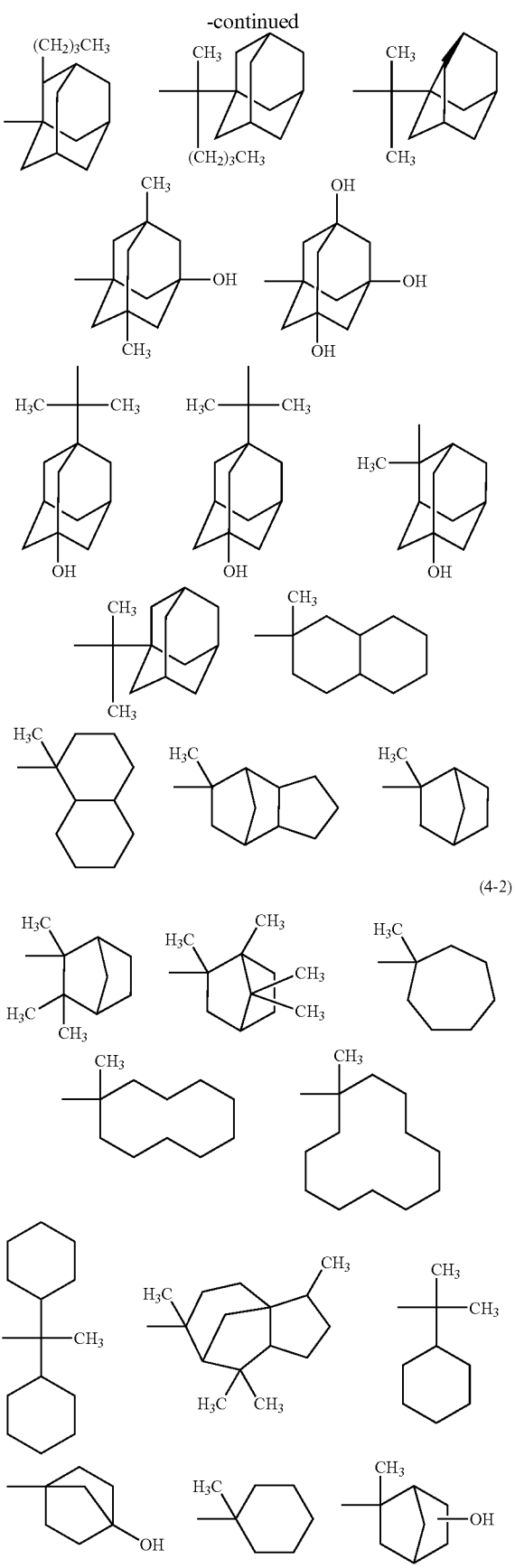

(4-1)

(4-2)

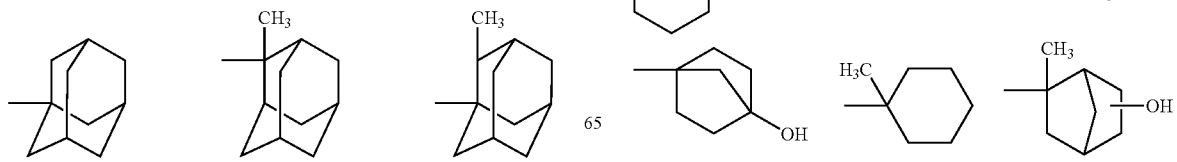

-continued

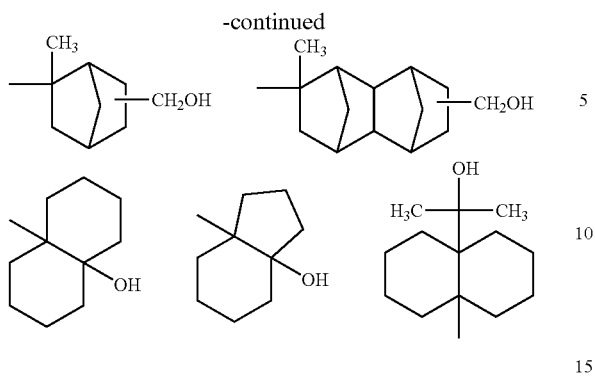

In the above formulas (4-1) and (4-2), methyl groups (CH$_3$) may independently be replaced with ethyl groups. As mentioned above, at least one of the ring carbons may have at least one substituent.

Examples of the silyl group SiR$^{13}$R$^{14}$R$^{15}$— include trimethylsilyl group, ethyldimethylsilyl group, methyldiethylsilyl group, triethylsilyl group, i-propyldimethylsilyl group, methyldi-i-propylsilyl group, tri-i-propylsilyl group, tert-butyldimethylsilyl group, methyldi-tert-butylsilyl group, tri-tert-butylsilyl group, phenyldimethylsilyl group, methyldiphenylsilyl group, and triphenylsilyl group.

Examples of the acyl group R$^{11}$—C(=O) include acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, and isonicotinoyl group. Furthermore, it is also possible to use ones in which fluorine atoms have been substituted for a part or entirety of hydrogen atoms of these acid-labile protecting groups.

The acid-labile protecting group R$^2$ containing a lactone ring is exemplified, as shown in the following formulas (5), (6) and (7).

(5)

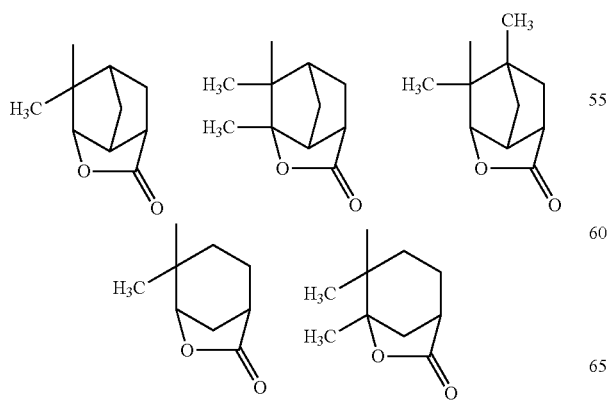

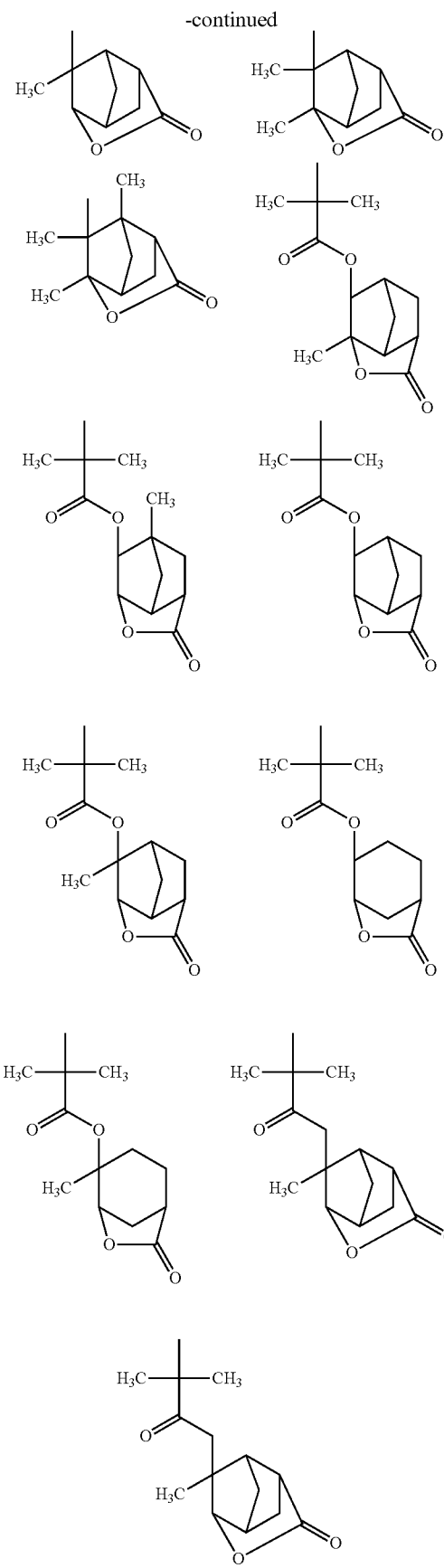

-continued

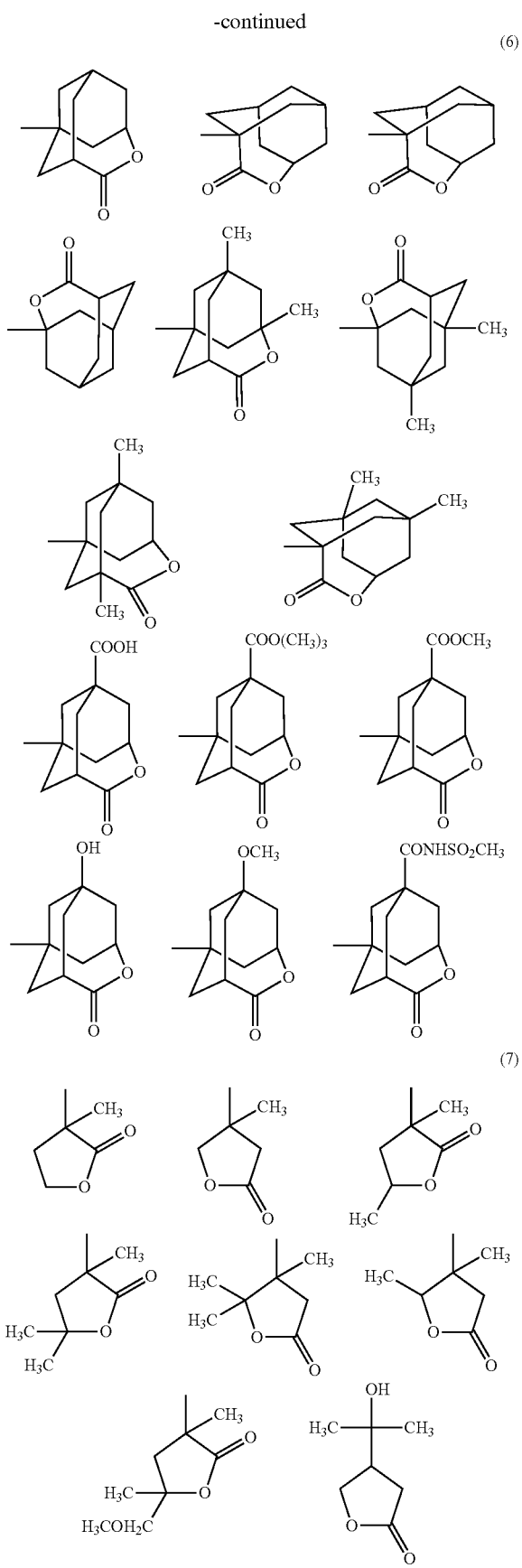

(6)

(7)

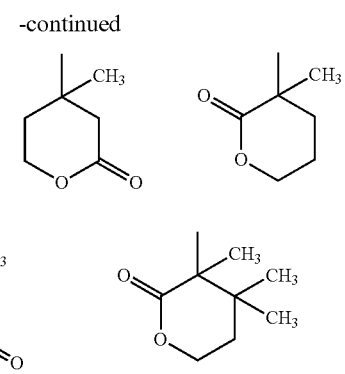

In formulas (5), (6) and (7), methyl groups (CH$_3$) may independently be replaced with ethyl groups.

In the case of using ArF excimer laser as a light source for exposure, preferable examples of the acid-labile protecting group R$^2$ are tertiary alkyl groups (e.g., tert-butyl group and tert-amyl group), alkoxyethyl groups (e.g., 1-ethoxyethyl group, 1-butoxyethyl group, 1-isobutoxyethyl group, and 1-cyclohexyloxyethyl group), and alkoxymethyl groups (e.g., methoxymethyl group and ethoxymethyl group), and moreover the above-mentioned alicyclic hydrocarbon groups (e.g., adamantyl group and isobornyl group), acid-labile protecting groups containing alicyclic hydrocarbon groups (e.g., 1-methylcyclopentane, methyladamantyl group, ethyladamantyl group, methylisobornyl group and ethylisobornyl group) and lactones.

The bivalent linking group W in formula (1) or (2) may be selected from a single bond, —(CR$^7$R$^8$)$_n$— (wherein n represents an integer of 1-10, each of R$^7$ and R$^8$ independently represents a monovalent organic group, and R$^7$ and R$^8$ may be combined to form a ring), —O—, —C(=O)—, —C(=O)O—, —O—C(=O)—, a bivalent alicyclic hydrocarbon group, a bivalent aromatic hydrocarbon group, a thioether group, an ester group, an amide group, a sulfonamide group, urethane group, a urea group, and combinations of these.

The bivalent alicyclic hydrocarbon group may be a group obtained by removing two hydrogen atoms from an alicyclic compound (e.g., norbornane and adamantane). The bivalent aromatic hydrocarbon group may be a group obtained by removing two hydrogen atoms from an aromatic compound (e.g., benzene).

The linking group W as a combination of the above-mentioned groups may be —(CR$^7$R$^8$)$_m$—C(=O)—O—(CR$^7$R$^8$)$_n$ or —(CR$^7$R$^8$)$_m$—(CR$^7$R$^8$)$_n$—, where each of m and n independently represents an integer of 0-10, m is preferably 0, n is preferably 1, and, when each of R$^7$ and R$^8$ is contained in a plural number, they may be the same or different.

The monovalent organic group R$^7$ or R$^8$ of the substituted methylene group —CR$^7$R$^8$— is not particularly limited. It may be a hydrogen atom, hydroxy group, or a C$_1$-C$_{30}$ monovalent organic group selected from alkyl groups, alicyclic hydrocarbon groups, substituted alkyl groups, alkoxy groups, aryl groups, and condensed polycyclic aromatic groups. These monovalent organic groups can have fluorine atom, oxygen atom, sulfur atom, nitrogen atom, and/or carbon-carbon double bond. Both of R$^7$ and R$^8$ may be the same or different. R$^7$ and R$^8$ may be combined to form a ring. This ring is preferably an alicyclic hydrocarbon group.

The alkyl group as R$^7$ or R$^8$ may be one having a carbon number of 1-30, preferably 1-12. For example, it is possible to cite methyl group, ethyl group, n-propyl group, i-propyl group, n-butyl group, 1-methylpropyl group, 2-methylpropyl group, tert-butyl group, n-pentyl group, i-pentyl group, 1,1-dimethylpropyl group, 1-methylbutyl group, 1,1-dimethylbutyl group, n-hexyl group, n-heptyl group, i-hexyl group, n-octyl group, i-octyl group, 2-ethylhexyl group, n-nonyl group, n-decyl group, n-undecyl group, and n-dodecyl group. Of these, lower alkyl groups are preferable. Particularly preferable ones are methyl group, ethyl group, n-propyl group, and i-propyl group.

Examples of the substituted alkyl group as $R^7$ or $R^8$ include ones in which at least one of hydrogen atoms of the alkyl group has been replaced with a $C_1$-$C_4$ alkoxy group, halogen atom, acyl group, acyloxy group, cyano group, hydroxyl group, carboxyl group, alkoxycarbonyl group, nitro group, or the like. A fluoroalkyl group in which at least one of hydrogen atoms of the alkyl group has been replaced with a fluorine atom(s) is preferable. Specific examples of the substituted alkyl group include lower fluoroalkyl groups such as trifluoromethyl group, pentafluoroethyl group, 2,2,2-trifluoroethyl group, n-heptafluoropropyl group, 2,2,3,3,3-pentafluoropropyl group, 3,3,3-trifluoropropyl group, and hexafluoroisopropyl group.

The alkoxy group as $R^7$ or $R^8$ may be a $C_1$-$C_4$ alkoxy group, such as methoxy group, ethoxy group, propoxy group, and butoxy group.

The aryl group as $R^7$ or $R^8$ may be a $C_1$-$C_{30}$ aryl group. As a monocyclic aryl group, it is preferable to use one having a ring carbon number of 3-12, more preferably 3-6. Examples include phenyl group, biphenyl group, terphenyl group, o-tolyl group, m-tolyl group, p-tolyl group, p-hydroxyphenyl group, p-methoxyphenyl group, mesityl group, o-cumenyl group, 2,3-xylyl group, 2,4-xylyl group, 2,5-xylyl group, 2,6-xylyl group, 3,4-xylyl group, 3,5-xylyl group, o-fluorophenyl group, m-fluorophenyl group, p-fluorophenyl group, o-trifluoromethylphenyl group, m-trifluoromethylphenyl group, p-trifluoromethylphenyl group, 2,3-bis(trifluoromethyl)phenyl group, 2,4-bis(trifluoromethyl)phenyl group, 2,5-bis(trifluoromethyl)phenyl group, 2,6-bis(trifluoromethyl)phenyl group, 3,4-bis(trifluoromethyl)phenyl group, 3,5-bis(trifluoromethyl)phenyl group, p-chlorophenyl group, p-bromophenyl group, and p-iodophenyl group.

The $C_1$-$C_{30}$, condensed polycyclic aromatic group as $R^7$ or $R^8$ may be a monovalent organic group, such as pentalenyl group, indenyl group, naphthyl group, azlenyl group, heptalenyl group, biphenylenyl group, indacenyl group, acenaphthylenyl group, fluorenyl group, phenarenyl group, phenanthryl group, anthryl group, fluoranthenyl group, acephenanthrylenyl group, aceanthrylenyl group, triphenylenyl group, pyrenyl group, chrysenyl group, naphthacenyl group, picenyl group, perylenyl group, pentaphenyl group, pentacenyl group, tetraphenylenyl group, hexaphenyl group, hexacenyl group, rubicenyl group, coronenyl group, trinaphthylenyl group, heptaphenyl group, heptacenyl group, pyranthrenyl group, and ovalenyl group. It is possible to cite ones in which at least one hydrogen atom of these groups has been replaced with a fluorine atom(s) or a $C_1$-$C_4$ alkyl or fluorine-containing alkyl group, as preferable ones.

Examples of a monocyclic or polycyclic, heterocyclic group as $R^7$ or $R^8$ having a ring atom number of 3-25 include pyridyl group, furyl group, thienyl group, pyranyl group, pyrrolyl group, thiantrenyl group, pyrazolyl group, isothiazolyl group, isoxazolyl group, pyrazinyl group, pyrimidinyl group, pyridadinyl group, tetrahydropyranyl group, tetrahydrofuranyl group, tetrahydrothiopyranyl group, tetrahydrothiofuranyl group, 3-tetrahydrothiophen-1,1-dioxide group, and heterocyclic groups in which at least one hydrogen atom of the ring has been replaced with an alkyl group, alicyclic hydrocarbon group, aryl group or heterocyclic group. Of these, ones having a monocyclic or polycyclic ether ring or lactone ring are preferable, such as the following,

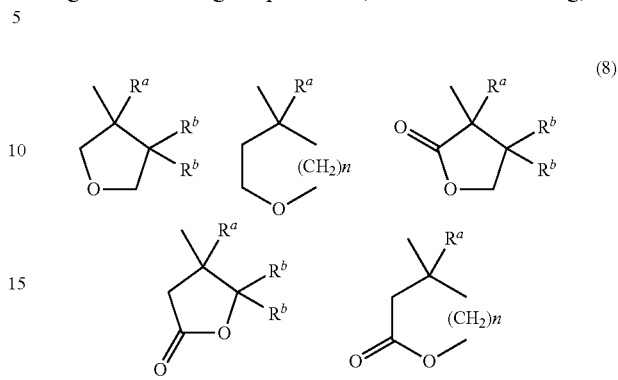

(8)

wherein each of $R^a$ and $R^b$ independently represents a hydrogen atom or $C_1$-$C_4$ alkyl group, and n represents an integer of 2-4.

As $R^7$ and $R^8$, a simple alicyclic hydrocarbon group or a combined alicyclic hydrocarbon group formed by simple alicyclic hydrocarbon groups that are combined together through carbon atoms may have a monocyclic or polycyclic structure. Specifically, these groups may have a monocyclo, bicyclo, tricyclo or tetracyclo structure of a carbon number of at least 3. The carbon number is preferably 3-30, more preferably 3-25. These alicyclic hydrocarbon groups may have substituents.

The alicyclic hydrocarbon group of monocyclic structure has a ring carbon number of preferably 3-12, more preferably 3-7. Its preferable examples include cyclopropyl group, cyclobutyl group, cyclopentyl group, cyclohexyl group, cycloheptyl group, cyclooctyl group, cyclodecanyl group, cyclododecanyl group, and 4-tert-butylcyclohexyl group. Examples of the alicyclic hydrocarbon group of polycyclic structure include those having a ring carbon number of 7-15, such as adamantyl group, noradamantyl group, decaline residue, tricyclodecanyl group, tetracyclododecanyl group, norbornyl group, and cedrol group. The alicyclic hydrocarbon group may be a spiro ring, preferably having a carbon number of 3-6. Its preferable examples include adamantyl group, decaline residue, norbornyl group, cedrol group, cyclohexyl group, cycloheptyl group, cyclooctyl group, cyclodecanyl group, cyclododecanyl group, and tricyclodecanyl group. At least one hydrogen atom of the ring carbons or linking groups of these organic groups may independently be replaced with at least one $C_1$-$C_{25}$ alkyl or substituted alkyl group, hydroxy group, alkoxy group, carboxyl group, alkoxycarbonyl group, or a group in which at least one hydrogen atom of these groups has been replaced with at least one fluorine atom or trifluoromethyl group.

The alkyl group is preferably a lower alkyl group, more preferably an alkyl group selected from methyl group, ethyl group, propyl group, and isopropyl group. The substituted alkyl group may have a substituent that is a hydroxy group, halogen atom or alkoxy group. The alkoxy group may be a $C_1$-$C_4$ alkoxy group such as methoxy group, ethoxy group, propoxy group and butoxy group. The alkoxycarbonyl group may be a methoxycarbonyl group, ethoxycarbonyl group, or isopropoxycarbonyl group.

Specifically, the linking group W may be a single bond, —O—, —C(=O)—O—, —CH$_2$—O—, —O—CH$_2$—, —CH$_2$—C(=O)—O—, —C(=O)—O—CH$_2$, —CH$_2$—

O—CH$_2$—, —CH$_2$—C(=O)—O—CH$_2$—, —C(=O)—O—CR$^7$R$^8$—, or —C$_6$H$_4$—O—CR$^7$R$^8$—. Herein, each of R$^7$ and R$^8$ is preferably and independently a hydrogen atom, fluorine atom, alkyl group, substituted alkyl group, or alicyclic hydrocarbon group. At least one hydrogen atom of these groups may be replaced with at least one fluorine atom. Of these examples, a more preferable one is —C(=O)—O—CR$^7$R$^8$— where each of R$^7$ and R$^8$ is independently a hydrogen atom or lower alkyl group.

A structure of the fluorine-containing polymer compound is derived from the polymerizable double-bond containing group and is represented by formula (9),

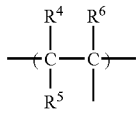

(9)

where each of R$^4$ and R$^6$ is independently a hydrogen atom, alkyl group or alicyclic hydrocarbon group. R$^5$ represents a hydrogen atom, cyano group, halogen atom, or alkyl group.

This alkyl group may be a substituted or unsubstituted one having a carbon atom number of 1-4. Examples of the alkyl group include methyl group, ethyl group, n-propyl group, isopropyl group, n-butyl group, isobutyl group, sec-butyl group, and tert-butyl group. The alkyl group may have a substituent that is a C$_1$-C$_4$ alkoxy group, halogen atom, acyl group, acyloxy group, cyano group, hydroxy group, carboxyl group, alkoxycarbonyl group, or nitro group.

The polymerizable double-bond containing group R$^1$ of the fluorine-containing compound represented by formula (1) may be (a) a C$_2$-C$_{10}$ alkenyl group, such as vinyl group, allyl group, isopropenyl group, 1-propenyl group, 1-butenyl group, 1-pentenyl group, 1-methyl-1-propenyl group, 1-methyl-1-butenyl group, 2-methyl-1-butenyl group, 1-methyl-1-pentenyl group, 2-methyl-1-pentenyl group, 3-methyl-1-pentenyl group, and 4-methyl-1-pentenyl group; (b) a C$_2$-C$_{10}$ fluorine-containing alkenyl group, such as perfluoroallyl group, 3-trifluoromethyl-2-propenyl group, 1-perfluorobutenyl group, 1-perfluoropentenyl group, 1-trifluoromethyl-1-butenyl group, 2-trilfluoromethyl-1-butenyl group, 3-trifluoromethyl-1-butenyl group, and 4-trifluoromethyl-1-butenyl group; or (c) a C$_2$-C$_{10}$ alkenyl group having a substituent that is a substituted or unsubstituted phenyl group, such as 1-phenyl-1-propenyl group, 2-phenyl-1-propenyl group, 3-phenyl-1-propenyl group, 1-phenyl-1-butenyl group, 3-phenyl-1-butenyl group, and 4-phenyl-1-butenyl group; or (d) a C$_2$-C$_{10}$ alkenyl group having a substituent that is an alicyclic hydrocarbon group, cycloether group, lactone group, or an alicyclic hydrocarbon group that is a norbornene skeleton, norbornane skeleton, isobornyl skeleton, tricyclodecane skeleton, tetracyclododecane skeleton, adamantane skeleton, or the like.

As R$^4$, R$^5$ or R$^6$, a simple alicyclic hydrocarbon group or a combined alicyclic hydrocarbon group formed by simple alicyclic hydrocarbon groups that are combined together through carbon atoms may have a monocyclic or polycyclic structure. Specifically, these groups may have a monocyclo, bicyclo, tricyclo or tetracyclo structure of a carbon number of at least 5. The carbon number is preferably 6-30, more preferably 7-25. These alicyclic hydrocarbon groups may have substituents.

Examples of the alicyclic hydrocarbon group of R$^4$, R$^5$ or R$^6$ may be the same as those of that of R$^7$ or R$^8$.

In the structure represented by formula (9) of the fluorine-containing polymer compound, two of R$^4$, R$^5$ and R$^6$ may be combined together, thereby forming the following exemplary ring structure represented by formula (10),

(10)

where R$^5$ represents a hydrogen atom, cyano group, halogen atom, or alkyl group; and A represents a group containing two carbon atoms C—C combined together, for forming an alicyclic structure.

This alicyclic structure may have a C$_3$-C$_{10}$ monocyclic or polycyclic structure, such as cyclopentane, cyclohexane, cycloheptane, norbornane, or a structure in which at least one hydrogen atom of these structures has been replaced with at least one lower alkyl or lower fluoroalkyl group.

Furthermore, the polymerizable double-bond containing group R$^1$ of the fluorine-containing compound may have a structure represented by the following formula (10-1) or (10-2) or a structure of vinylphenyl group,

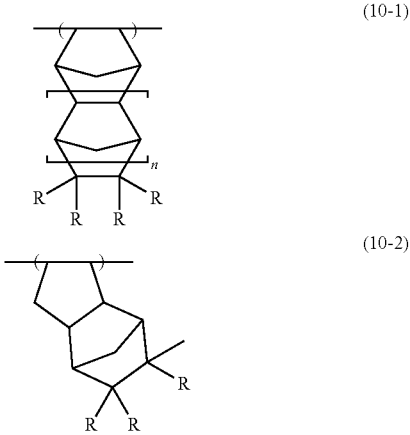

where formulas (10-1) and (10-2) are shown in the form of repeating unit after cleavage of the double bond, each of R's independently represents a hydrogen atom, halogen atom, or cyano group, and n represents an integer of 1-4.

The polymerizable double-bond containing group R$^1$ of the fluorine-containing compound is preferably a structure represented by CH$_2$=CH—, CH$_2$=C(CH$_3$)—, CH$_2$=C(CF$_3$)— or CH$_2$=C(CH$_2$OH)—, or a structure represented by one of the following formulas (10-3) to (10-6),

(10-3)

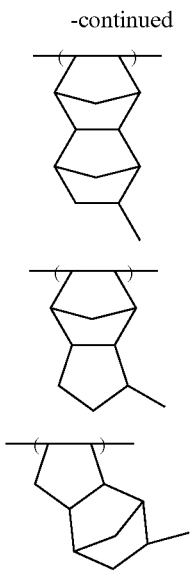

where formulas (10-3) to (10-6) are shown in repeating unit after cleavage of the double bond. Of these, $CH_2=CH-$, $CH_2=C(CH_3)-$, and $CH_2=C(CF_3)-$ are more preferable, and $CH_2=C(CH_3)-$ is still more preferable.

It is preferable that the following partial structure (9-1)

where all of the symbols are defined as in formula (2), contained in the repeating unit (a) represented by formula (2) has a structure obtained by cleavage of the polymerizable double-bond of a group selected from vinyloxy group, allyloxy group, acryloyloxy group, methacryloyloxy group, α,α,α-trifluoroacryloyloxy group, norbornoyloxy group, and vinylphenoxy group, which are respectively shown as follows.

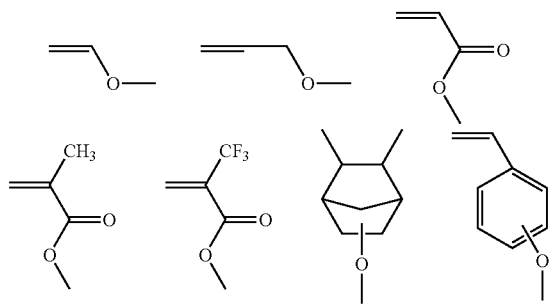

The fluorine-containing compound represented by formula (1) may have a formula selected from the following most preferable exemplary formulas,

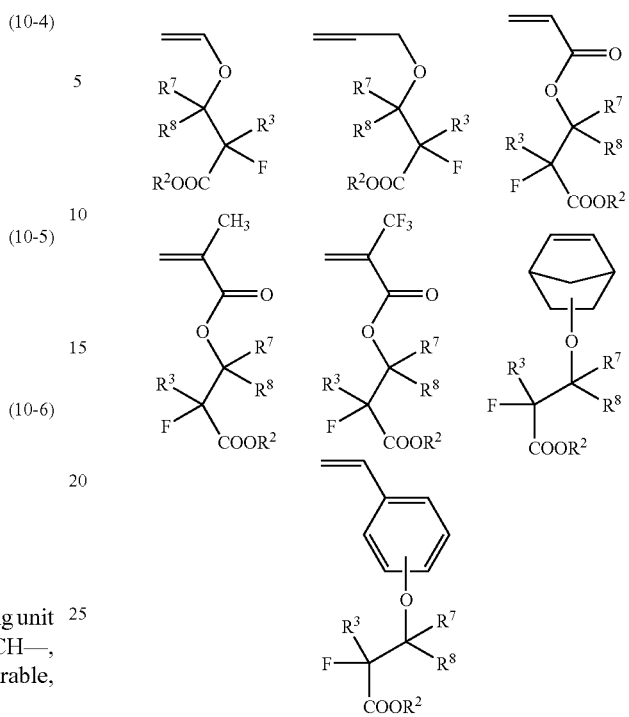

wherein $R^2$ represents an acid-labile protecting group, $R^3$ represents a fluorine atom or trifluoromethyl group, $R^7$ represents a hydrogen atom or a straight-chain, branched or cyclic alkyl or fluoroalkyl group, $R^8$ represents a straight-chain, branched or cyclic alkyl or fluoroalkyl group, and $R^7$ and $R^8$ may be combined to form a ring.

In the above formulas, $R^3$ is particularly preferably a fluorine atom. The alkyl or fluoroalkyl group of $R^7$ and $R^8$ is preferably a lower alkyl or lower fluoroalkyl group. It is preferable that the alkyl group is a cyclic alkyl group. It is preferable that $R^7$ represents a hydrogen atom. It is particularly preferable that $R^3$ represents a fluorine atom, $R^7$ represents a hydrogen atom or lower alkyl group, and $R^8$ represents a lower alkyl group. It is also preferable that $R^3$ represents a fluorine atom, and $R^7$ and $R^8$ are bonded together to form a lower alicyclic hydrocarbon group.

In the fluorine-containing polymer compound of the present invention, the molar ratio (copolymerization ratio) of the repeating unit (a) to the repeating unit (b) derived from another copolymerizable monomer (comonomer) can suitably be set for adjusting resist dry etching resistance, standard developing solution suitability, adhesion to substrate, resist profile, and resolving power, heat resistance, sensitivity and the like, which are general properties required for resists. The above-mentioned another copolymerizable monomer is described in detail hereinafter in the section of "ANOTHER COMONOMER".

The fluorine-containing polymer compound of the present invention may be a homopolymer of the repeating unit (a) or a copolymer in which the molar ratio of the repeating unit (a) to the repeating unit (b) is 0.1-99.9%:99.9-0.1%, 1-99%:99-1%, or 10-90%:90-10%, preferably 30-70%:70:30%, based on the total mol number of the repeating units (a) and (b). If the repeating unit (a) is in less than 0.1%, solubility upon development may become inferior. If it is in greater than 99.9%, solubility adjustment may become difficult.

It is preferable that the repeating unit (b) derived from another comonomer is a first repeating unit derived from an acrylic or methacrylic ester having a lactone group or a second repeating unit derived from an acrylic or methacrylic ester having a polar group. In this case, the content of the first repeating unit in the fluorine-containing polymer compound is preferably 10-60 mol %, more preferably 20-50 mol %. The content of the second repeating unit therein is preferably 1-50 mol %, more preferably 5-30 mol %. Furthermore, the fluorine-containing polymer compound may contain a third repeating unit that contains no acid-labile protecting group and is derived from an acrylic or methacrylic ester with none of a polar group and a lactone group. In this case, the content of the third repeating unit therein is preferably 1-70 mol %, more preferably 5-60 mol %.

The fluorine-containing polymer compound of the present invention may be 1,000-1,000,000, preferably 2,000-500,000, in weight average molecular weight determined by gel permeation chromatography (GPC). If it is less than 1,000, the resist film may become insufficient in strength. If it is greater than 1,000,000, solubility in solvent may become too low. With this, it may become difficult to obtain a flat resist film. Dispersibility (Mw/Mn where Mw represents weight average molecular weight, and Mn represents number average molecular weight) is preferably 1.01-5.00, more preferably 1.01-4.00, particularly preferably 1.01-3.00, the most preferably 1.10-2.50.

The process for polymerizing the fluorine-containing compound is not particularly limited, as long as it is one generally used. It is preferable to use radical polymerization or ion polymerization. In some cases, it is also possible to use coordination anion polymerization, living anion polymerization, cation polymerization, ring-opening metathesis polymerization, vinylene polymerization or vinyl addition polymerization.

The radical polymerization may be conducted by a known polymerization method, such as bulk polymerization, solution polymerization, suspension polymerization or emulsion polymerization, in the presence of a radical polymerization initiator or radical initiating source, with a batch-wise, half-continuous or continuous operation.

The radical polymerization initiator is not particularly limited. As its examples, azo compounds, peroxide compounds and redox compounds are cited. In particular, preferable examples include azobisbutyronitrile, t-butylperoxypivalate, di-t-butylperoxide, i-butyrylperoxide, lauroylperoxide, succinic acid peroxide, dicinnamylperoxide, di-n-propylperoxydicarbonate, t-butylperoxyallyl monocarbonate, benzoyl peroxide, hydrogen peroxide, and ammonium persulfate.

The reaction vessel used in the polymerization reaction is not particularly limited. Furthermore, a polymerization solvent may be used in the polymerization reaction. As the polymerization solvent, one that does not interfere with the radical polymerization is preferable. Representative ones are ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Furthermore, it is also possible to use solvents such as water, ethers, cyclic ethers, fluorohydrocarbons, and aromatics. These solvents can be used singly or in combination of at least two types. Furthermore, it may be accompanied in use with a molecular weight adjusting agent such as mercaptan. The reaction temperature of the polymerization reaction is suitably changed, depending on the radical polymerization initiator or radical polymerization initiating source. In general, 20-200° C. is preferable. In particular, 30-140° C. is preferable.

It is possible to remove organic solvent or water from the obtained solution or dispersion of the fluorine-containing polymer compound by reprecipitation, filtration, heating distillation under reduced pressure, or the like.

Fluorine-Containing Monomer

The repeating unit represented by formula (2) of the fluorine-containing polymer compound is formed by the production of a bivalent group through cleavage of the polymerizable double bond of the fluorine-containing compound (monomer) represented by formula (1). Thus, the above description in the section of "FLUORINE-CONTAINING POLYMER COMPOUND" with respect to the polymerizable double bond for forming the chain skeleton moiety, the group containing the polymerizable double bond, each organic group, the linking group W, the acid-labile protecting group $R^2$ and the like corresponds directly to that of the fluorine-containing monomer and therefore is not repeated herein.

The process for producing the fluorine-containing compound represented by formula (1) is not particularly limited. For example, it can be produced by a process represented by the following reaction formulas [1] to [4],

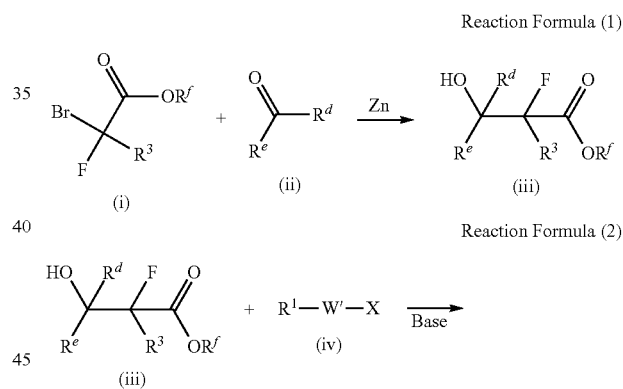

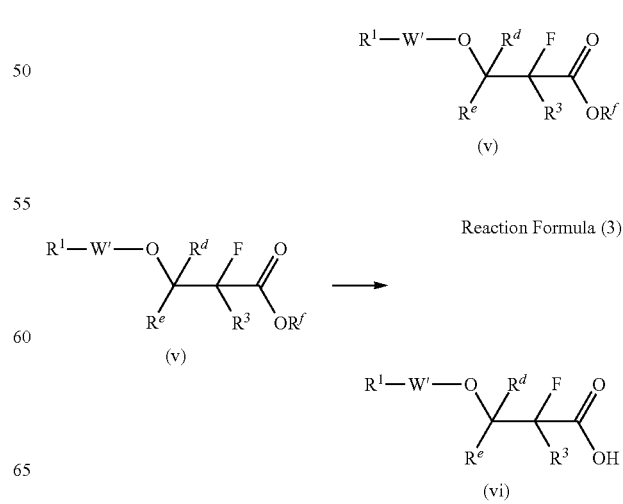

-continued

Reaction Formula (4)

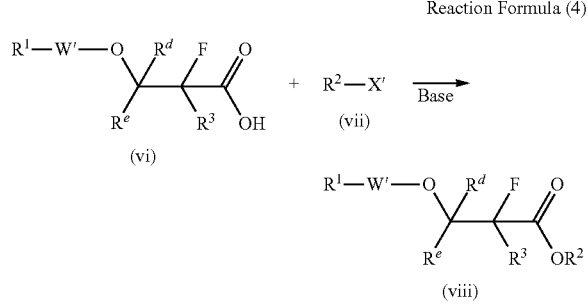

where $R^1$, $R^2$ and $R^3$ are defined as in formula (1); $R^d$ represents a hydrogen atom or monovalent organic group, and each of $R^e$ and $R^f$ independently represents a monovalent organic group; each of X and X' independently represents a halogen atom, trifluoromethanesulfonate group, $C_1$-$C_4$ alkylsulfonate group or arylsulfonate group; W' represents a bivalent linking group; and W'—O—$CR^dR^e$ corresponds to W in formula (1).

As each of $R^d$ and $R^e$ corresponds to $R^7$ or $R^8$, detailed description of $R^d$ and $R^e$ is the same as that of $R^7$ and $R^8$. The monovalent organic group as $R^d$, $R^e$ or $R^f$ is preferably a lower alkyl or fluoroalkyl group, such as methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group. It is more preferable that $R^d$ and $R^e$ are bonded together to form a cyclopentyl group, cyclohexyl group, or cycloheptyl group.

The above process represented by reaction formulas [1] to [4] is described in detail, as follows. At first, as shown in reaction formula [1], a fluorine-containing carboxylate (i) having an active halogen atom at α-position is reacted with a carbonyl compound (ii) in the presence of Zn under an anhydrous condition (Reformatsky reaction), thereby obtaining a hydroxy carboxylate (iii). Then, as shown in reaction formula [2], the hydroxy carboxylate (iii) is reacted in solvent with a halogen compound (iv) having a polymerizable double bond in the presence of a base, thereby obtaining an unsaturated carboxylate (v). Then, as shown in reaction formula [3], the carboxylate (v) is hydrolyzed into an unsaturated carboxylic acid (vi) having a fluorine atom at α-position. At last, the obtained unsaturated carboxylic acid (vi) is reacted in solvent with a halogen compound (vii) in the presence of a base, thereby obtaining a fluorine-containing compound (viii). It is clear that formula (viii) corresponds to formula (1) if "W'—O—$CR^dR^e$" is interpreted as W.

The solvent used in the reaction of reaction formulas [1], [2] or [4] is not particularly limited, as long as it is not active in the reaction. Its examples include aliphatic hydrocarbons such as pentane, hexane and heptane; aromatic hydrocarbons such as benzene, toluene and xylene; nitriles such as acetonitrile, propionitrile, phenylacetonitrile, isobutyronitrile, and benzonitrile; acid amides such as dimethylformamide, dimethylacetamide, methylformamide, formamide, and hexamethylphosphoric triamide, lower ethers such as tetrahydrofuran, 1,2-dimethoxyethane, 1,4-dioxane, diethyl ether, 1,2-epoxyethane, 1,4-dioxane, dibutyl ether, tert-butyl methyl ether, and substituted tetrahydrofurans. Of these dimethylformamide and tetrahydrofuran are preferable. These solvents can be used in combination. The amount of the solvent may be about 1-100 parts by weight, preferably 1-10 parts by weight, relative to one part by weight of the starting material.

It is preferable to remove water as much as possible from the solvent to be used in the reaction of reaction formula [1]. The water content of this solvent is more preferably 50 ppm or less.

It is also preferable to remove water as much as possible from the solvent to be used in the reaction of reaction formulas [2] or [4]. It is, however, not necessary to completely remove water from this solvent. Its water content close to that is generally contained in an industrially available solvent is not problematic in conducting the reaction. Therefore, such solvent can be used without removing water.

It is preferable to activate zinc by a known method for its use in the reaction of reaction formula [1]. Its exemplary methods include a method using metallic zinc obtained by reducing a zinc salt (e.g., zinc chloride) with potassium, magnesium, lithium or the like; a method for activating metallic zinc by treating metallic zinc with hydrochloric acid; a method for activating zinc by treating metallic zinc with a copper salt or silver salt in acetic acid to convert metallic zinc into an alloy of zinc and copper or silver; a method for activating zinc by ultrasonic waves; a method for activating zinc by mixing metallic zinc with chlorotrimethylsilane in ether; and a method for activating zinc by bringing metallic zinc into contact with chlooromethylsilane and a copper compound in an aprotic organic solvent.

Zinc may have any form, such as powder, granule, aggregate, porous form, cutting scrap, or filament. The reaction temperature for conducting the reaction of reaction formula [1] may be about –78 to 120° C. Its reaction time may be 10 minutes to 20 hours for convenience, although it varies depending on the reaction agents. Its reaction pressure may be around ordinary pressure. Its other reaction conditions may be the same as those of known analogous reactions using metallic zinc therein.

Examples of the base used in the reactions of reaction formulas [2] and [4] include organic bases, such as trimethylamine, triethylamine, diisopropylethylamine, tri-n-propylamine, tri-n-butylamine, dimethyllaurylamine, dimethylaminopyridine, N,N-dimethylaniline, dimethylbenzylamine, 1,8-diazabicyclo[5,4,0]undec-7-ene, 1,4-diazabicyclo[2,2,2]octane, pyridine, 2,4,6-trimethylpyridine, pyrimidine, pyridazine, 3,5-lutidine, 2,6-lutidine, 2,4-lutidine, 2,5-lutidine, and 3,4-lutidine. Of these, triethylamine, diisopropylethylamine, dimethylaminopyridine, 1,8-diazabicyclo[5,4,0]undec-7-ene, pyridine, and 2,6-lutidine are preferable.

The amount of the base to be used in the reaction of reaction formula [2] or [4] may be 1 mol or greater, generally preferably 1-10 moles, particularly more preferably 1-5 moles, per mol of the substrate.

Similar to the reaction of reaction formula [1], the reaction temperature for conducting the reactions of reaction formulas [2] to [4] may be about –78 to 120° C. Their reaction time may be 10 minutes to 20 hours for convenience, although it varies depending on the reaction agents. Their reaction pressure may be around ordinary pressure. Their other reaction conditions may be the same as those of known analogous reactions.

The reaction of reaction formula [3] is conducted by hydrolyzing the substrate (v) with water in the presence of a basic substance that may be the above-mentioned organic base or an inorganic basic substance (e.g., sodium hydroxide, potassium hydroxide, sodium carbonate, and calcium hydroxide).

It is possible to conduct a purification operation (e.g., washing, separation of solvent, etc., and drying) after each reaction of reaction formulas [1] to [4].

In case that a fluorine-containing carboxylate having an acid-labile protecting group is available (i.e., $R^f = R^2$ in formula (i)), it is possible to obtain the target fluorine-containing compound represented by formula (viii) by conducting only the two reactions of reaction formulas [1] and [2].

Other Comonomers

The fluorine-containing polymer compound of the present invention is obtained by homopolymerization of the fluorine-containing compound represented by formula (1) or by its copolymerization with at least one polymerizable monomer (comonomer). In this polymerization, cleavage of the C=C double bond of the polymerizable double-bond containing group $R^1$ of the fluorine-containing compound occurs to form the skeleton of the fluorine-containing polymer compound, but the rest of the structure of the fluorine-containing compound does not change.

Besides the repeating unit (a) represented by formula (2), the fluorine-containing polymer compound can contain various repeating units for the purpose of adjusting dry etching resistance, standard developing solution suitability, adhesion to substrate, resist profile, and general characteristics (e.g., resolution, heat resistance and sensitivity) necessary for resist.

Such repeating units may be those corresponding to the after-mentioned monomers, but are not limited to those. By containing such repeating units, it is possible to achieve fine adjustments of qualities necessary for the resin, particularly (1) solubility in coating solvent, (2) film forming property (glass transition point), (3) alkali development property, (4) film decrease upon alkali development (hydrophilic or hydrophobic property and alkali-soluble group selection), (5) adhesion of the unexposed portion to substrate, and (6) dry etching resistance.

Examples of other comonomers copolymerizable with the fluorine-containing compound include the following compounds [1], [2] and [3].

[1] polymerizable compounds represented by formula (1) where $R^2$ represents a monovalent organic group containing no acid-labile protecting group;

[2] polymerizable compounds represented by formula (1) where α-opposition atom of the carboxylic moiety (COOR$^2$) has at least one hydrogen atom; and

[3] polymerizable compounds represented by formula of $R^1$—W—Y where $R^1$ and W are defined as in formula (1) and Y represents a monovalent organic group containing no acid-labile protecting group.

The acid-labile protecting group in the compounds [1]-[3] is defined as in the fluorine-containing polymer compound. The above description with respect to the monovalent organic groups $R^1$, $R^3$, $R^4$, $R^5$ and $R^6$ and the bivalent linking group W corresponds directly to that of the compounds [1] and [2] and therefore is not repeated herein.

Examples of the compounds [3] include acrylates, fluorine-containing acrylates, methacrylates, fluorine-containing methacrylates, styrene compounds, fluorine-containing styrene compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds, fluorine-containing norbornene compounds, sulfur dioxide, and vinyl silanes. At least one monomer selected from these can be copolymerized with the fluorine-containing compound.

The above acrylates and methacrylates are not particularly limited with respect to their ester moiety. Their examples include alkyl esters of acrylic acid or methacrylic acid, such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, tert-butyl acrylate or methacrylate, amyl acrylate or methacrylate, n-hexyl acrylate or methacrylate, n-octyl acrylate or methacrylate, 2-ethylhexyl acrylate or methacrylate, benzyl acrylate or methacrylate, chlorobenzyl acrylate or methacrylate, octyl acrylate or methacrylate, 2-hydroxyethyl acrylate or methacrylate, 4-hydroxybutyl acrylate or methacrylate, 5-hydroxypentyl acrylate or methacrylate, 2,2-dimethyl-3-hydroxypropyl acrylate or methacrylate, trimethylolpropane monoacrylate or methacrylate, pentaerythritol monoacrylate or methacrylate, furfuryl acrylate or methacrylate, tetrahydrofurfuryl acrylate or methacrylate, lauryl acrylate or methacrylate, and 2-hydroxypropyl acrylate or methacrylate; acrylate or methacrylate containing an ethylene glycol, propylene glycol or tetramethylene glycol group; 3-oxocyclohexylacrylate or methacrylate, adamantyl acrylate or methacrylate, alkyladamantyl acrylate or methacrylate, cyclohexyl acrylate or methacrylate, tricyclodecanyl acrylate or methacrylate, and acrylates or methacrylates containing a ring structure (e.g., norbornene ring); and the above-mentioned acrylates containing a trifluoromethyl group or cyano group at α-position.

The fluorine-containing acrylates or methacrylates contain fluorine at their ester moiety and may have a cyano group at their α-position. It is possible to use without a particular limitation fluorine-containing acrylates or methacrylates in which a part of the ester moiety of the above-mentioned acrylates or methacrylates has been fluorinated. In other words, they are acrylates or methacrylates having at their ester moiety a fluorine-containing alkyl group or a fluorine-containing ring structure (e.g., fluorine-containing benzene ring, fluorine-containing cyclopentane ring, fluorine-containing cyclohexane ring, fluorine-containing cycloheptane ring, fluorine-containing norbornel group, and fluorine-containing adamantyl group) in which at least one hydrogen at their ring carbon(s) has been replaced with at least one fluorine atom or fluorine-containing alkyl group (e.g., trifluoromethyl group). Furthermore, it is also possible to use acrylates or methacrylates having at their ester moiety a fluorine-containing tert-butyl ester or a cyclohexyl group or norbornyl group containing a hexafluoroisopropanol group substituted.

Furthermore, preferable comonomers include an acrylate, methacrylate or α,α,α-trifluoroacrylate containing a lactone group. This lactone group may be any group containing a lactone structure. It is preferably a group containing a five to seven-membered lactone structure. It is preferably a group having a ring-fused structure (e.g., bicyclo structure and spiro structure) formed by a combination of another ring structure with a five to seven-membered lactone structure. By containing a lactone ring, the resulting resist is improved in line edge roughness and development defect.

The above lactone group may be selected from the structures represented by the following formulas (12-1) and (12-2),

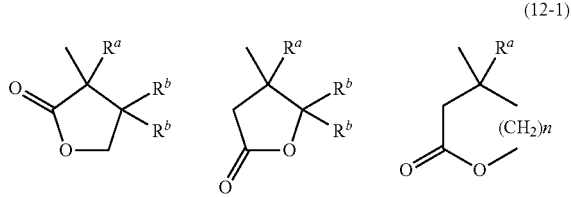

(12-1)

where $R^a$ represents a $C_1$-$C_4$ alkyl group or perfluoroalkyl group, each of $R^b$ independently represents a hydrogen atom, a $C_1$-$C_4$ alkyl group or perfluoroalkyl group, a hydroxy group, a carboxyl group, an alkyloxycarbonyl group, an alkoxy group or the like, and n represents an integer of 1-4, (12-2)

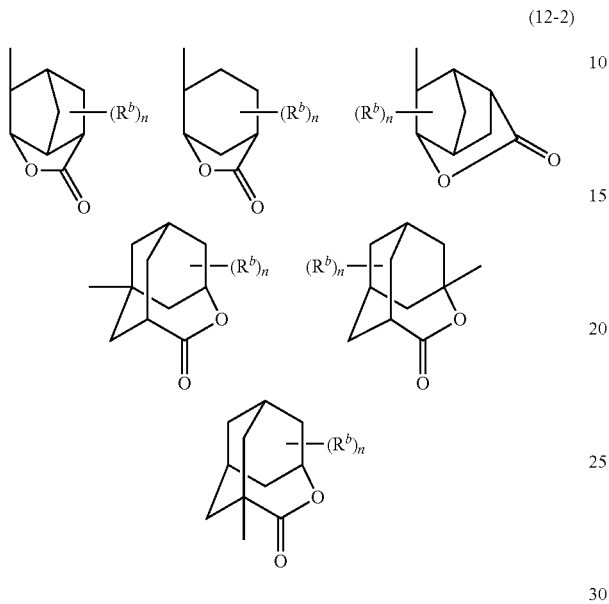

where each of $R^b$ independently represents a hydrogen atom, a $C_1$-$C_4$ alkyl group or perfluoroalkyl group, a hydroxy group, a carboxyl group, an alkyloxycarbonyl group, an alkoxy group or the like, and n represents an integer of 1-4.

Specific examples of the lactone group include the following formulas (13-1) to (13-6).

(13-1)

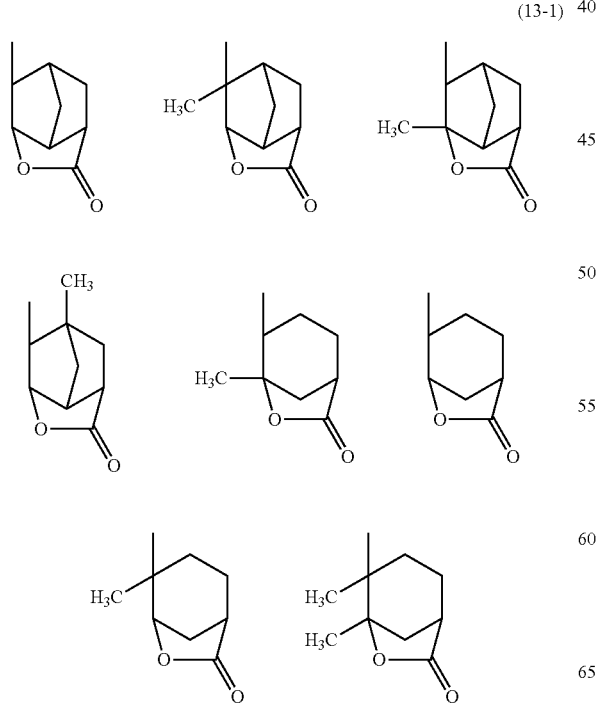

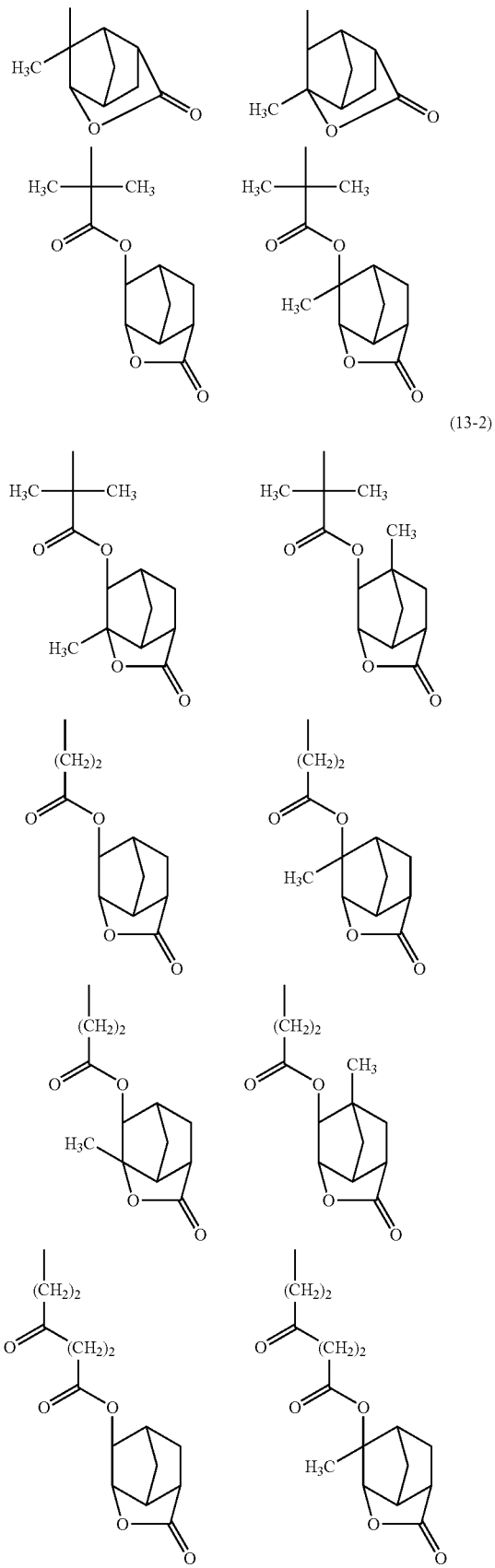

(13-2)

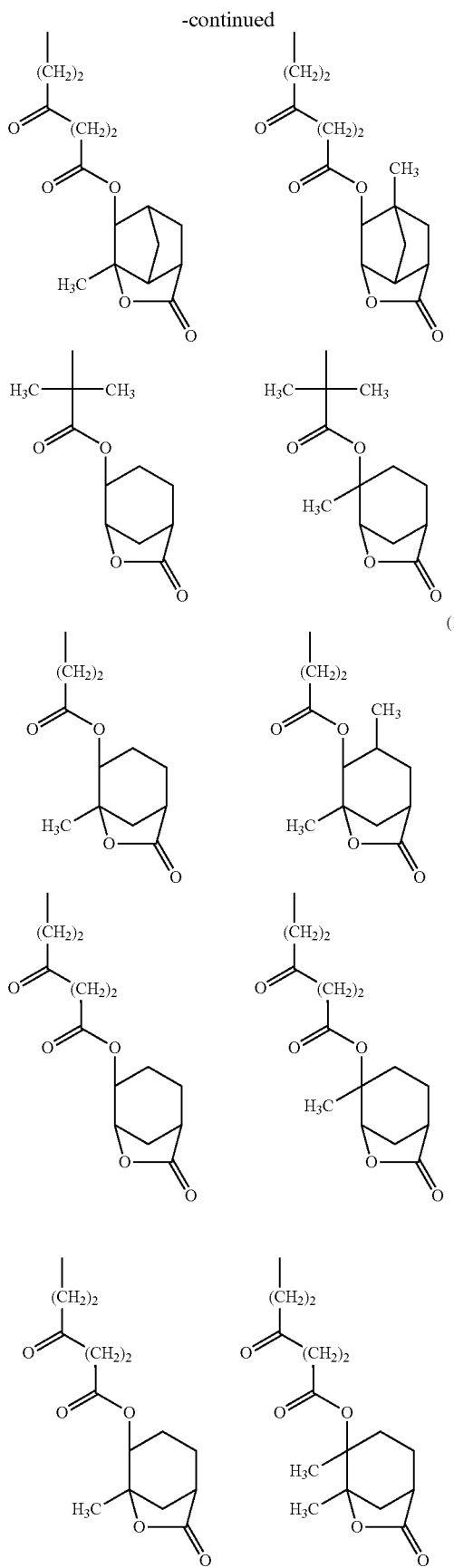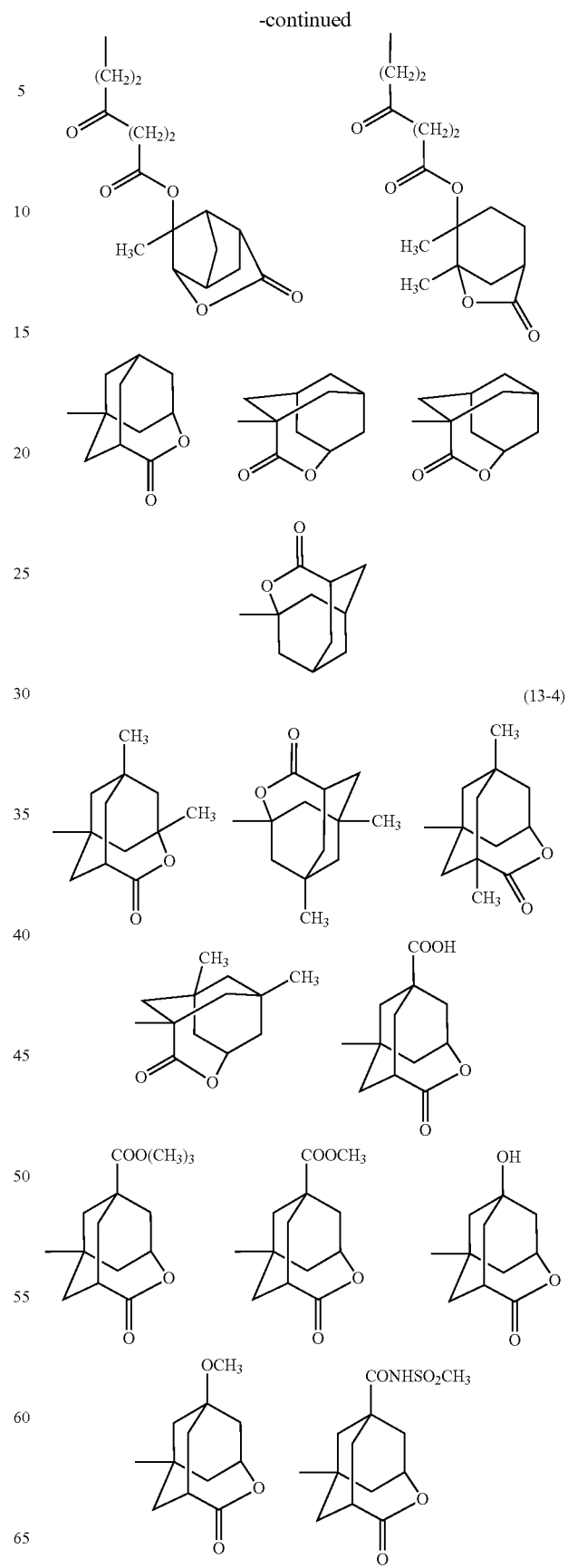

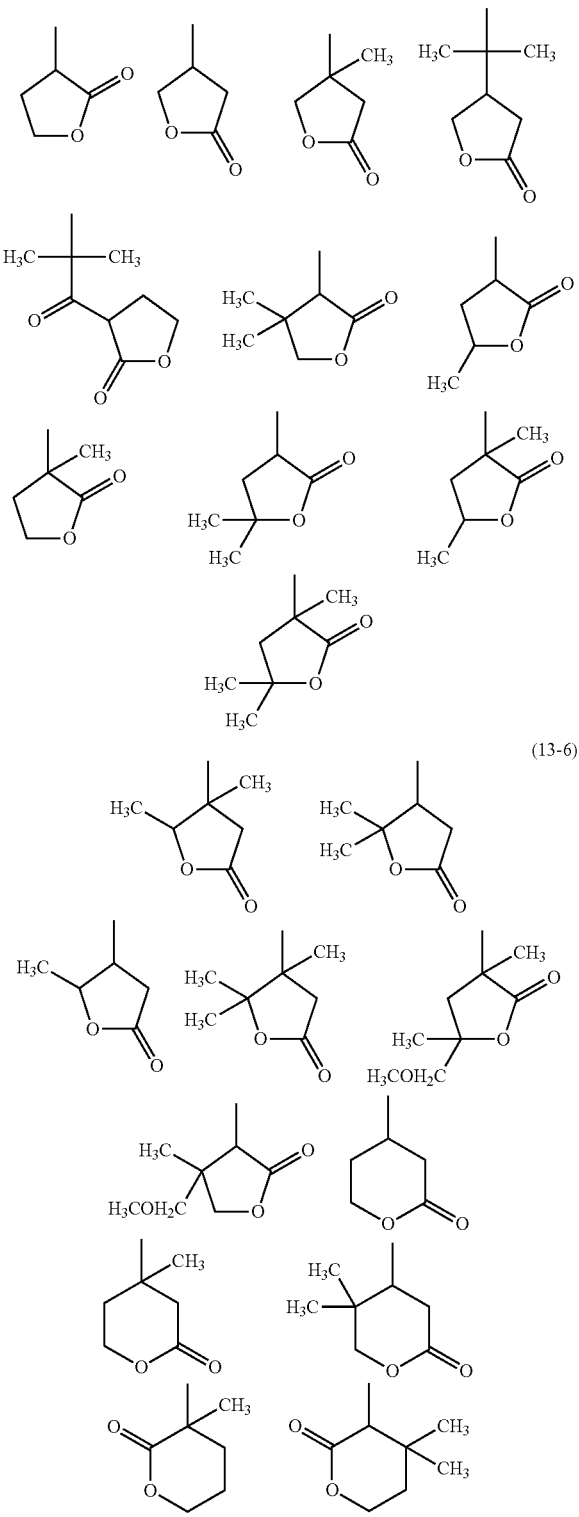

In the formulas (13-1) to (13-6), methyl groups ($CH_3$) may independently be replaced with ethyl groups.

The vinyl ethers or allyl ethers as the comonomers may be those having a $C_1$-$C_{30}$ alkyl group, fluoroalkyl group or alicyclic hydrocarbon group as a substituent. These groups preferably contain a halogen atom, hydroxy group, amino group, aryl group, alkyl group or alicyclic hydrocarbon group as a substituent. The vinyl ethers and allyl ethers are exemplified, as follows.

Specific examples of alkyl vinyl ether include methyl vinyl ether, ethyl vinyl ether, propyl vinyl ether, isopropyl vinyl ether, butyl vinyl ether, isobutyl vinyl ether, sec-butyl vinyl ether, tert-butyl vinyl ether, pentyl vinyl ether, hexyl vinyl ether, octyl vinyl ether, decyl vinyl ether, and dodecyl vinyl ether. Those of cyclic vinyl ether include cyclopentyl vinyl ether, cyclohexyl vinyl ether, norbornyl vinyl ether, adamantyl vinyl ether, and butyllactone group-containing vinyl ether. Those of perfluoroalkyl vinyl ether include perfluoromethyl vinyl ether, perfluoroethyl vinyl ether, perfluoropropyl vinyl ether, perfluoroisopropyl vinyl ether, perfluorobutyl vinyl ether, perfluoroisobutyl vinyl ether, perfluoro-sec-butyl vinyl ether, perfluoro-tert-butyl vinyl ether, perfluoropentyl vinyl ether, perfluorohexyl vinyl ether, perfluorooctyl vinyl ether, and perfluorododecyl vinyl ether. Those of hydroxy group-containing vinyl ether include hydroxymethyl vinyl ether, 2-hydroxyethyl vinyl ether, 3-hydroxypropyl vinyl ether, 4-hydroxybutyl vinyl ether, 5-hydroxypentyl vinyl ether, 6-hydroxyhexyl vinyl ether, diethylene glycol monovinyl ether, polyethylene glycol monovinyl ether, and 1,4-cyclohexanedimethanol vinyl ether. Further specific examples of vinyl ether include ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, diethylene glycol vinyl ether, dimethylaminoethyl vinyl ether, diethylaminoethyl vinyl ether, butylaminoethyl vinyl ether, benzyl vinyl ether, and tetrahydrofurfuryl vinyl ether.

Specific examples of allyl ethers include methyl allyl ether, ethyl allyl ether, propyl allyl ether, butyl allyl ether, benzyl allyl ether, and cyclohexyl allyl ether. Those of hydroxy group-containing allyl ethers include alkylene glycol monoallyl ethers such as ethylene glycol monoallyl ether, propylene glycol monoallyl ether, diethylene glycol monoallyl ether, polyethylene glycol monoallyl ether, and hydroxybutyl allyl ether; and allyl ethers of polyhydric alcohols such as glycerol monoallyl ether.

Further examples include epoxy group-containing vinyl ethers and allyl ethers. As a β-ketoester group containing vinyl ether or allyl ether, it is possible to cite allyl acetoacetate. Furthermore, it is possible to cite silicon-containing vinyl ethers having a hydrolyzable group, such as trimethoxysilyl vinyl ether.

Specific examples of allyl esters include allyl acetate, allyl caproate, allyl caprylate, allyl laurate, allyl palmitate, allyl stearate, allyl benzoate, allyl acetoacetate, and allyl lactate.

Specific examples of vinyl esters include vinyl butyrate, vinyl isobutyrate, vinyl trimethylacetate, vinyl diethylacetate, vinyl valerate, vinyl caproate, vinyl chloroacetate, vinyl dichloroacetate, vinyl methoxyacetate, vinyl butoxyacetate, vinyl acetoacetate, vinyl lactate, vinyl β-phenylbutyrate, and vinyl cyclohexylcarboxylate.

Further examples include dialkyl itaconates, such as dimethyl itaconate, diethyl itaconate and dibutyl itaconate; dialkyl fumarates or monoalkyl fumarates, such as dibutyl fumarate; and alkyl vinyl acetates such as ethyl vinyl acetate.

Specific examples of olefins include ethylene, propylene and cyclohexene. Those of fluorine-containing olefins include vinyl fluoride, vinylidene fluoride, trifluoroethylene, chlorotrifluoroethylene, tetrafluoroethylene, hexafluoropropylene, hexafluoroisobutene, and octafluorocyclopentene.

A styrene compound usable in the present invention is a compound in which a vinyl group is bonded to an aromatic ring. Its specific examples include styrene, m- or p-methoxystyrene, m- or p-ethoxystyrene, m- or p-propoxystyrene, m- or p-isopropoxystyrene, m- or p-butoxystyrene, m- or p-tert-butoxystyrene, m- or p-(1-ethoxyethoxy)styrene, m- or p-(1-ethoxypropoxy)styrene, m- or p-(1-isobutoxyethoxy)styrene, m- or p-(2-tetrahydropyranyloxy)styrene, m- or p-tert-butoxycarbonyloxystyrene, m- or p-acetoxystyrene, m- or p-propionyloxystyrene, m- or p-pivaloyloxystyrene, m- or p-benzoyloxystyrene, m- or p-mesyloxystyrene, m- or p-phenylsulfonyloxystyrene, and m- or p-tosyloxystyrene. These styrene compounds may have at their α-position a halogen atom, alkyl group or fluorine-containing alkyl group.

In the case of introducing the structure of a styrene compound into the fluorine-containing polymer compound, for example, p-butoxycarbonyloxystyrene is copolymerized with the fluorine-containing compound, and then the butoxycarbonyl moiety may be converted into a hydroxy group.

The norbornene compounds or fluorine-containing norbornene compounds are norbornene monomers having a monocyclic or polycyclic structure. In the invention, it is preferable to use a norbornene compound or fluorine-containing norbornene compound obtained by Diels Alder addition reaction between an unsaturated compound (e.g., fluorine-containing olefins, allyl alcohol, fluorine-containing allyl alcohols, acrylic acid, α-fluoroacrylic acid, methacrylic acid, vinyl esters, fluorine-containing vinyl esters, and acrylates, methacrylates, fluorine-containing acrylates and fluorine-containing methacrylates, which are exemplified hereinbefore) and cyclopentadiene or cyclohexadiene.

Specific examples of the acrylamide or methacryloamides include unsaturated amides such as acrylamide, methacrylamide, N-alkylacrylamide or methacryloamide, where alkyl group is $C_1$-$C_{10}$ one (e.g., methyl group, ethyl group, propyl group, butyl group, tert-butyl group, heptyl group, octyl group, cyclohexyl group, and hydroxyethyl group), N,N-dialkylacrylamide or acryloamide, where alkyl group is $C_1$-$C_{10}$ one (e.g., methyl group, ethyl group, butyl group, isobutyl group, ethylhexyl group, and cyclohexyl group), N-hydroxyethyl-N-methylacrylamide or methacryloamide, N-methylolacrylamide, N-methylolmethacrylamide, and diacetoneacrylamide.

Further examples of other comonomers include acrylic acid, methacrylic acid, vinylsulfonic acid, maleic acid, fumaric acid, crotonic acid, itaconic acid, maleimide, acrylonitrile, methacrylonitrile, maleilonitrile, an alkoxysilyl group-containing vinyl silane, and allyloxyethanol.

To conduct a copolymerization for producing the fluorine-containing polymer compound represented by formula (2), it is preferable to use at least one of the above-explained acrylates, fluorine-containing acrylates, methacrylates, fluorine-containing methacrylates, styrene compounds, and fluorine-containing styrene compounds.

Other comonomers are not particularly limited, as long as they are copolymerizable with the fluorine-containing compound represented by formula (1). For exposure with a high energy ray of 300 nm or shorter, they are preferably free from multiple bond and aromatic ring.

Solvent

As a process for forming the fluorine-containing polymer compound according to the present invention into a thin film, it is possible to use a process having the steps of dissolving the fluorine-containing polymer compound in an organic solvent, applying the coating solution to a substrate, and drying the film. The organic solvent is not particularly limited, as long as the fluorine-containing polymer compound is soluble therein. Examples of the organic solvent include (a) ketones such as acetone, methyl ethyl ketone, cyclohexanone, methyl isoamyl ketone, and 2-heptanone; (b) polyhydric alcohols and their derivatives such as ethylene glycol, ethylene glycol monoacetate, diethylene glycol, diethylene glycol monoacetate, propylene glycol, propylene glycol monoacetate, dipropylene glycol, and monomethyl ether, monoethyl ether, monopropyl ether, monobutyl ether or monophenyl ether of dipropylene glycol monoacetate; (c) cyclic ethers such as dioxane; (d) esters such as methyl lactate, ethyl lactate, methyl acetate, ethyl acetate, butyl acetate, methyl pyruvate, ethyl pyruvate, methyl methoxypropionate, and ethyl ethoxypropionate; (d) aromatic solvents such as xylene and toluene; (e) fluorine-containing solvents such as chlorofluorocarbons, alternatives for chlorofluorocarbons, perfluoro compounds, and hexafluoroisopropyl alcohol; (f) terpene-series petroleum naphtha solvents (high-boiling-point weak solvents) for improving coatability; and (g) paraffin-series solvents. These solvents may be used singly or in a mixture of at least two.

Acid Generator

An acid generator used for the resist composition of the present invention is not particularly limited. It is possible to select any one of those used as acid generators of chemically amplified resists. Examples of such acid generators include bissulfonyl diazomethanes, nitrobenzyl derivatives, onium salts, halogen-containing triazine compounds, cyano group-containing oximesulfonate compounds, and other oximesulfonate compounds. These photo acid generators may be used singly or in combination of at least two. Its content may normally be 0.5-20 parts by weight, relative to 100 parts by weight of the fluorine-containing polymer compound. If it is less than 0.5 parts by weight, image formation property may become insufficient. It is greater than 20 parts by weight, it may be difficult to prepare a homogeneous coating solution, and its storage stability tends to lower.

Surfactant

It is preferable to contain a surfactant, preferably at least one fluorine-containing and/or silicon-containing surfactant, in the resist composition of the present invention. The containment of such surfactant is particularly effective in case that a pattern line width is very narrow upon using an exposure light source of 250 nm or shorter, particularly 220 nm or shorter, thereby making a resist pattern with good sensitivity, good resolution, good adhesion to substrate, and fewer development defects.

Pattern Forming Method

A conventional resist pattern forming method can be used as a method for using the resist material of the present invention. That is, firstly a solution of the resist material is applied to a substrate such as silicon wafer with a spinner, followed by drying to form a photosensitive layer. This is exposed to a high-energy ray by an exposure apparatus or the like through a desired mask pattern, followed by heating. Then, this is subjected to a development treatment using a developing solution, for example, an alkali aqueous solution such as 0.1-10 wt % tetramethylammonium hydroxide aqueous solution. This forming method makes it possible to obtain a pattern conforming to the mask pattern. Furthermore, according to need, it is possible to contain additives that are miscible with the resist material, for example, various additives such as additional resins, quencher, plasticizer, stabilizer, coloring agent, surfactant, tackifier, leveling agent, defoaming agent, compatibility enhancing agent, adhesion enhancing agent, and antioxidant.

A high-energy ray used in the present invention is not particularly limited. In particular, in the case of conducting a fine processing, it is effective to use an exposure device equipped with a short-wavelength high-energy ray (e.g., $F_2$ excimer laser, ArF excimer laser, KrF excimer laser, or soft X-ray) generating source. It is effective to use an immersion exposure device that makes it possible to conduct a more efficient fine processing in numerical aperture and effective wavelength by using a medium (e.g., water and fluorine-containing solvents), into which the used high-energy ray has a less absorption, at a part of the optical path. The present resist material is also preferable in the case of use in this device.

EXAMPLE 1

Synthesis of ethyl 2,2-difluoro-3-hydroxy pentanoate Represented by the Following Formula

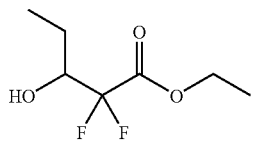

A 500 mL reactor was charged with 24.2 g (370 mmol, 1.3 eq) of activated metallic zinc and 300 mL of tetrahydrofuran (THF) (dehydrated one), followed by adding in a dropwise manner an ethyl bromo-difluoro acetate/THF solution prepared by adding 51.47 g (253.6 mmol, 1.0 eq) of ethyl bromo-difluoro acetate to 80 mL of THF (dehydrated one). After the dropping, stirring was conducted at room temperature for 20 minutes, followed by adding a propionaldehyde/THF solution prepared by adding 14.80 g (254.8 mmol, 1.0 eq) of propionaldehyde to 80 mL of THF (dehydrated one), and then stirring at room temperature for 30 minutes. Then, water and diisopropyl ether were added, followed by separation of an organic layer from an aqueous layer. The obtained organic layer was washed with diluted hydrochloric acid and water, followed by removing water with magnesium sulfate, filtration, and distilling the diisopropyl ether off, thereby obtaining 41.2 g of the target ethyl 2,2-difluoro-3-hydroxy pentanoate. The yield was 89%.

The property of ethyl 2,2-difluoro-3-hydroxy pentanoate was as follows.

$^1$H NMR (CDCl$_3$) d 4.31 (q, J=7.1 Hz, 2H; CH$_2$—O), 3.89 (m, 1H; CH—OH), 2.50 (br, 1H; OH), 1.71 (m, 1H), 1.52 (m, 1H), 1.32 (t, J=7.1 Hz, 3H; CH$_3$), 1.02 (t, J=7.3 Hz, 3H; CH$_3$)

$^{19}$F NMR (CDCl$_3$) d −115.26 (d, J=252 Hz, 1F), −122.95 (d, J=252 Hz, 1F)

EXAMPLE 2

Production of 1-ethoxycarbonyl-1,1-difluoro-2-butyl methacrylate Represented by the Following Formula

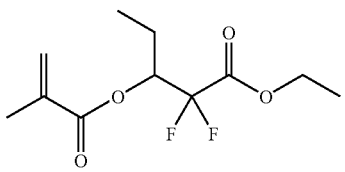

A 25 ml reactor was charged with 1.50 g (8.2 mmol) of ethyl 2,2-difluoro-3-hydroxypentanoate, 6.5 g of chloroform, 10 mg of an antioxidant NONFLEX MBP made by Seiko Chemical Co., Ltd., 1.03 g (9.9 mmol, 1.2 eq) of methacrylic chloride, and 1.25 g (12.4 mmol, 1.5 eq) of triethylamine, followed by stirring at 55° C. for 4 hours. Then, 10 g of water was added, followed by extraction with chloroform one time. The obtained organic layer was washed with diluted hydrochloric acid and water, followed by removing water with magnesium sulfate. After conducting filtration, chloroform was distilled off, thereby obtaining 2.06 g of the target 1-ethoxycarbonyl-1,1-difluoro-2-butyl methacrylate. Purity was 66%, and yield was 66%.

The property of 1-ethoxycarbonyl-1,1-difluoro-2-butyl methacrylate was as follows.

$^1$H NMR (CDCl$_3$) d 6.14 (s, 1H; methylene), 5.62 (s, 1H; methylene), 5.35 (m, 1H; CH—O), 4.27 (m, 2H; CH$_2$—O), 1.93 (s, 3H; CH$_3$), 1.81 (m, 2H; CH$_2$), 1.28 (t, J=7.2 Hz, 3H; CH$_3$), 0.95 (t, J=7.6 Hz, 3H; CH$_3$)

$^{19}$F NMR (CDCl$_3$) d −113.63 (d, J=264 Hz, 1F), −119.57 (d, J=264 Hz, 1F)

EXAMPLE 3

Production of 1-hydroxycarbonyl-1,1-difluoro-2-butyl methacrylate, methacrylic acid (1), Represented by the Following Formula

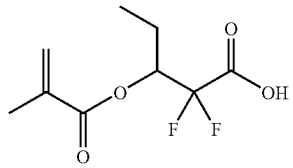

A 25 mL reactor was charged with 1.00 g (2.6 mmol) of 1-ethoxycarbonyl-1,1-difluoro-2-butyl methacrylate (purity: 66%) and 1.00 g of water, followed by cooling to 0° C., adding 1.06 g (4.0 mmol, 1.5 eq) of 15 wt % sodium hydroxide aqueous solution in a dropwise manner, and then stirring at room temperature for 1 hr. The reaction solution was washed with 10 g of diisopropyl ether. The obtained aqueous layer was washed with diluted hydrochloric acid, followed by extraction with diisopropyl ether two times, removal of water with magnesium sulfate, filtration, and then distilling diisopropyl ether off, thereby obtaining 0.19 g of the target methacrylic acid (1). Upon this, purity was 78%, and yield was 27%.

The property of methacrylic acid (1) was as follows.

$^1$H NMR (CDCl$_3$) d 7.24 (br, 1H; COOH), 6.16 (s, 1H; methylene), 5.63 (s, 1H; methylene), 5.39 (m, 1H; CH—O), 1.93 (s, 3H; CH$_3$), 1.85 (m, 2H; CH$_2$), 0.97 (t, J=7.6 Hz, 3H; CH$_3$)

$^{19}$F NMR (CDCl$_3$) d −114.24 (d, J=264 Hz, 1F), −119.48 (d, J=264 Hz, 1F)

EXAMPLE 4

Production of 1-(methoxymethyl)oxycarbonyl-1,1-difluoro-2-butyl methacrylate, methacrylate (1), Represented by the Following Formula

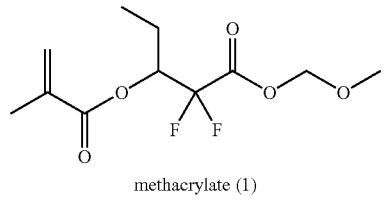

methacrylate (1)

Under nitrogen, a 20 mL reactor was charged with 70 mg (0.25 mmol) of 1-hydroxycarbonyl-1,1-difluoro-2-butyl methacrylate (purity: 78%) and 3 mL of THF (dehydrated one), followed by cooling to 0° C. Then, 65 μL (0.47 mmol, 1.9 eq) was added, followed by stirring at 0° C. for 10 min. Then, 30 μL (0.40 mmol, 1.6 eq) of chloromethyl methyl ether was added, followed by stirring at 0° C. for 20 min. Then, 5 mL of water was added to the reaction solution, followed by extraction with diisopropyl ether two times and removal of water with magnesium sulfate. After conducting filtration, diisopropyl ether was distilled off, thereby obtaining 58 mg of the target 1-(methoxymethyl)oxycarbonyl-1,1-difluoro-2-butyl methacrylate. Upon this, purity was 96%, and yield was 83%.

The property of 1-(methoxymethyl)oxycarbonyl-1,1-difluoro-2-butyl methacrylate was as follows.

$^1$H NMR (CDCl$_3$) d6.15 (m, 1H; methylene), 5.63 (m, 1H; methylene), 5.30-5.45 (m, 3H, CH—O, CH$_2$), 3.47 (s, 3H; CH$_3$), 1.93 (s, 3H; CH$_3$), 1.85 (m, 2H; CH$_2$), 0.97 (t, J=7.6 Hz, 3H; CH$_3$)

$^{19}$F NMR (CDCl$_3$) d −113.62 (d, J=264 Hz, 1F), −119.51 (d, J=264 Hz, 1F)

$^{13}$C NMR (CDCl$_3$) d 9.7, 18.5, 21.2, 58.6, 73.0, 93.2, 113.6, 127.4, 135.5, 162.7, 166.3

EXAMPLE 5

Production of t-butyl 2,2-difluoro-3-hydroxypentanoate Represented by the Following Formula

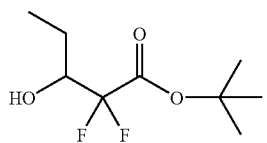

A 100 mL reactor was charged with 2.10 g (32.1 mmol, 1.5 eq) of activated metallic zinc and 30 mL of THF (dehydrated one), followed by adding in a dropwise manner a t-butyl bromo-difluoro acetate/THF solution prepared by adding 5.0 g (21.6 mmol, 1.0 eq) of t-butyl bromo-difluoro acetate to 10 mL of THF (dehydrated one). After the dropping, stirring was conducted at room temperature for 1 hr, followed by adding a propionaldehyde/THF solution prepared by adding 1.25 g (21.5 mmol, 1.0 eq) of propionaldehyde to 10 mL of THF (dehydrated one), and then stirring at room temperature for 30 minutes. Then, water and diisopropyl ether were added, followed by separation of an organic layer from an aqueous layer. The obtained organic layer was washed with diluted hydrochloric acid and water, followed by removing water with magnesium sulfate, filtration, and distilling the diisopropyl ether off, thereby obtaining 3.59 g of the target t-butyl 2,2-difluoro-3-hydroxy pentanoate. Upon this, purity was 80%, and yield was 70%.

The property of t-butyl 2,2-difluoro-3-hydroxy pentanoate was as follows.

$^1$H NMR (CDCl$_3$) d 3.85 (m, 1H; CH—OH), 2.80 (br, 1H; OH), 1.60 (m, 2H; CH$_2$), 1.50 (m, 9H; CH$_3$), 1.02 (t, J=7.6 Hz, 3H; CH$_3$)

$^{19}$F NMR (CDCl$_3$) d −115.87 (dd, J=7.3 Hz, 261 Hz, 1F), −122.47 (dd, J=14.6 Hz, 263 Hz, 1F)

EXAMPLE 6

Production of 1-(t-butoxycarbonyl)-1,1-difluoro-2-butyl methacrylate, methacrylate (2), Represented by the Following Formula

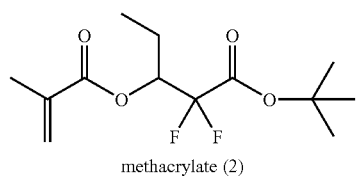

methacrylate (2)

A 25 mL reactor was charged with 1.50 g (5.6 mmol) of t-butyl 2,2-difluoro-3-hydroxypentanoate and 15 mL of chloroform, 10 mg of NONFLEX MBP, 1.17 g (11.2 mmol, 2 eq) of methacrylic chloride, and 0.87 g (8.6 mmol, 1.5 eq) of triethylamine, followed by stirring at 55° C. for 24 hr. Then, 15 mL of water was added, followed by extraction with chloroform one time. The obtained organic layer was washed with saturated sodium hydrogencarbonate and water, followed by removal of water with magnesium sulfate. After conducting filtration, chloroform was distilled off, thereby obtaining 1.57 g of the target 1-(t-butoxycarbonyl)-1,1-difluoro-2-butyl methacrylate. Upon this, purity was 58%, and yield was 58%.

The property of 1-(t-butoxycarbonyl)-1,1-difluoro-2-butyl methacrylate was as follows.

$^1$H NMR (CDCl$_3$) d 6.15 (s, 1H; methylene), 5.62 (m, 1H; methylene), 5.36 (m, 1H; CH—O), 1.93 (s, 3H; CH$_3$), 1.78 (m, 2H; CH$_2$), 1.46 (s, 3H; CH$_3$), 0.95 (t, J=7.6 Hz, 3H; CH$_3$)

$^{19}$F NMR (CDCl$_3$) d −113.15 (dd, J=7.3 Hz, 261 Hz, 1F), −120.17 (dd, J=14.6 Hz, 261 Hz, 1F)

Example 7

Synthesis of Fluorine-Containing Polymer Compound (1), as Shown in the Following Formula

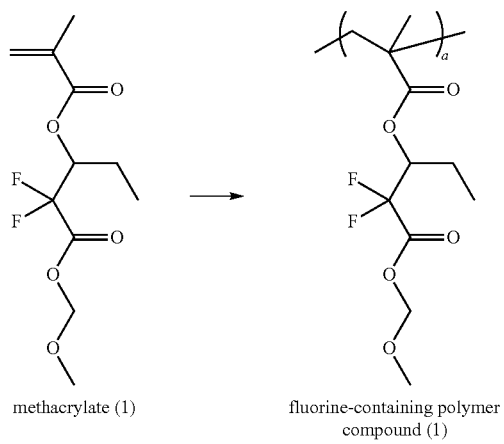

methacrylate (1)   fluorine-containing polymer compound (1)

A 100 mL round-bottom flask equipped with a reflux condenser and a stirrer was charged with 6.00 g of methacrylate (1), 0.11 g of azobisisobutyronitrile (AIBN), and 15.0 mL of methyl ethyl ketone, followed by replacing the inside of the flask with nitrogen. While the flask was heated in an oil bath at 60° C., stirring was conducted for 18 hr to conduct the reaction. After the reaction, 60 ml of n-hexane was added, followed by stirring. The resulting precipitate was taken out of the flask, followed by drying at 55° C. for 18 hr, thereby obtaining 4.40 g of fluorine-containing polymer compound (1) in a white solid. Yield was 73%. The molecular weight was determined by gel permeation chromatography (GPC; standard substance: polystyrene). The results are shown in Table 1.

EXAMPLE 8

Synthesis of Fluorine-Containing Polymer Compound (2), as Shown in the Following Formula

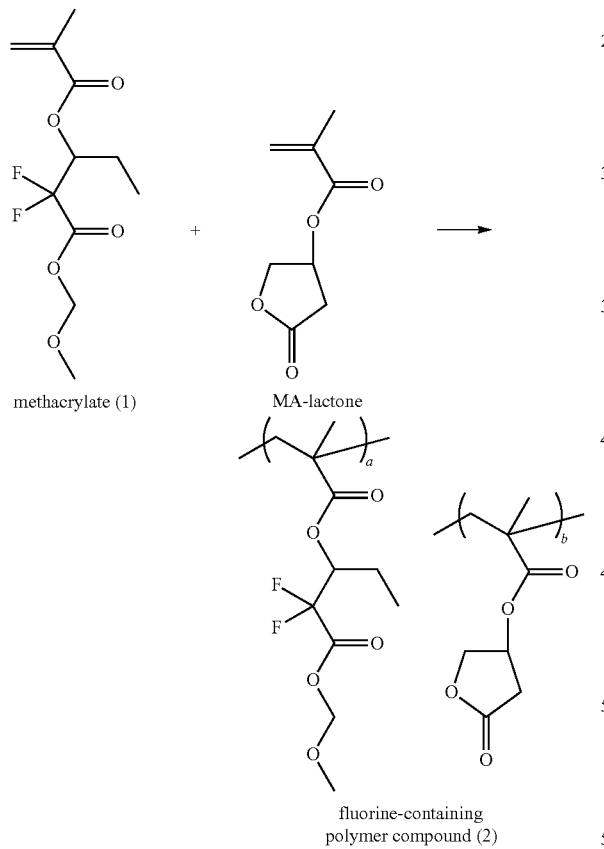

Similar to the process of Example 7, a copolymerization was conducted by using two raw materials, methacrylate (1) and MA-lactone (made by OSAKA ORGANIC CHEMICAL INDUSTRY LTD.), thereby synthesizing fluorine-containing polymer compound (2) in a white solid. The molecular weight was determined by GPC (standard substance: polystyrene). The compositional molar ratio (a/b) of fluorine-containing polymer compound (2) was determined by NMR. The results are shown in Table 1.

EXAMPLE 9

Synthesis of Fluorine-Containing Polymer Compound (3), as Shown in the Following Formula

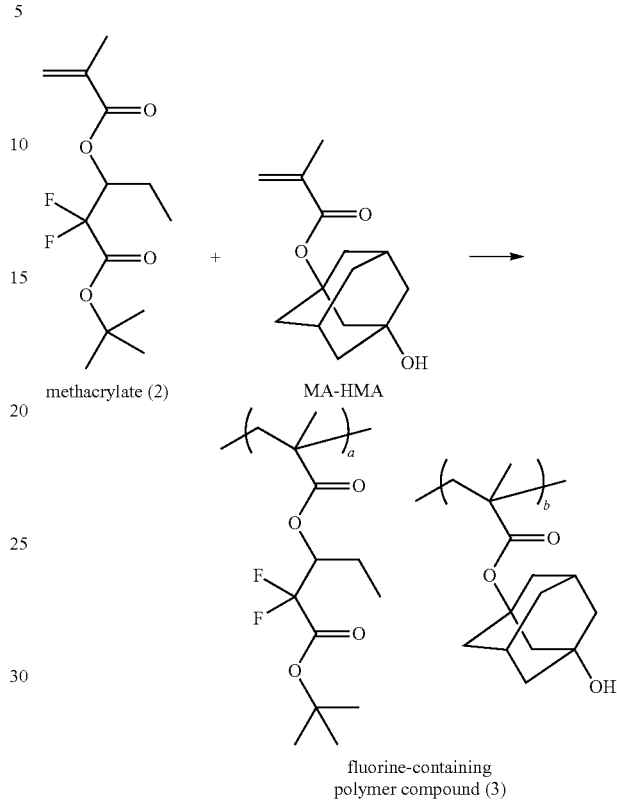

Similar to the process of Example 7, a copolymerization was conducted by using two raw materials, methacrylate (2) and hydroxyadamantyl methacrylate (MA-HMA made by DAICEL CHEMICAL INDUSTRIES, LTD.), thereby synthesizing fluorine-containing polymer compound (3) in a white solid. The molecular weight was determined by GPC (standard substance: polystyrene). The compositional molar ratio (a/b) of fluorine-containing polymer compound (3) was determined by NMR. The results are shown in Table 1.

EXAMPLE 10

Synthesis of Fluorine-Containing Polymer Compound (4), as Shown in the Following Formula

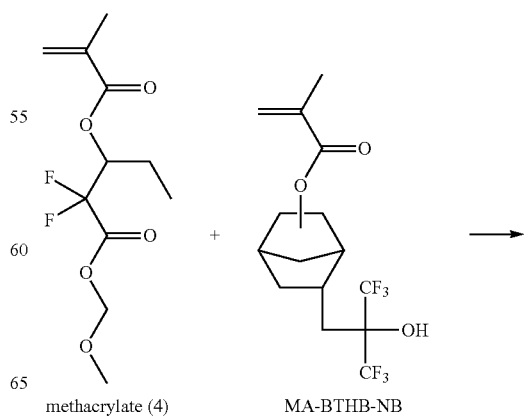

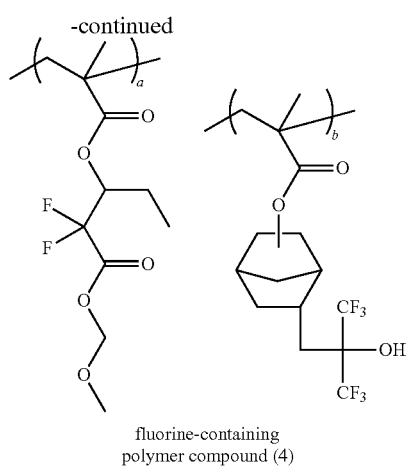

fluorine-containing
polymer compound (4)

Similar to the process of Example 7, a copolymerization was conducted by using two raw materials, methacrylate (1) and MA-BTHB-NB synthesized by the process according to Japanese Patent Application Publication 2004-175740, of which disclosure is incorporated herein by reference, thereby synthesizing fluorine-containing polymer compound (4) in a white solid. The molecular weight was determined by GPC (standard substance: polystyrene). The compositional molar ratio (a/b) of fluorine-containing polymer compound (4) was determined by NMR. The results are shown in Table 1.

EXAMPLE 11

1. Synthesis of MA-3,5-HFA-CHOH Represented by the Following Formula

A 2 L, three-necked flask equipped at its top with a reflux condenser was charged with 100 g of 3,5-HFA-CHOH, which had been synthesized by the process according to Japanese Patent Application Publication 2004-083900, corresponding to U.S. Pat. No. 7,125,943, of which disclosure is incorporated herein by reference, and which is represented by the following formula,

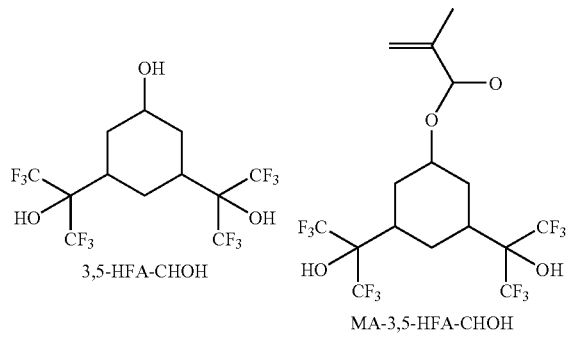

23.8 g of methacrylic acid, 22.0 g of methanesulfonic acid, and 500 mL of toluene, followed by heating under reflux in an oil bath at 130° C. for 3.5 hr. After the reaction, the reaction solution was poured into saturated sodium bicarbonate water for neutralization, followed by adding 1 L of toluene and collecting the toluene layer. The obtained toluene solution was concentrated, followed by recrystallization, thereby obtaining 78.0 g of MA-3,5-HFA-CHOH.

2. Synthesis of Fluorine-Containing Polymer Compound (5), As Shown in the Following Formula

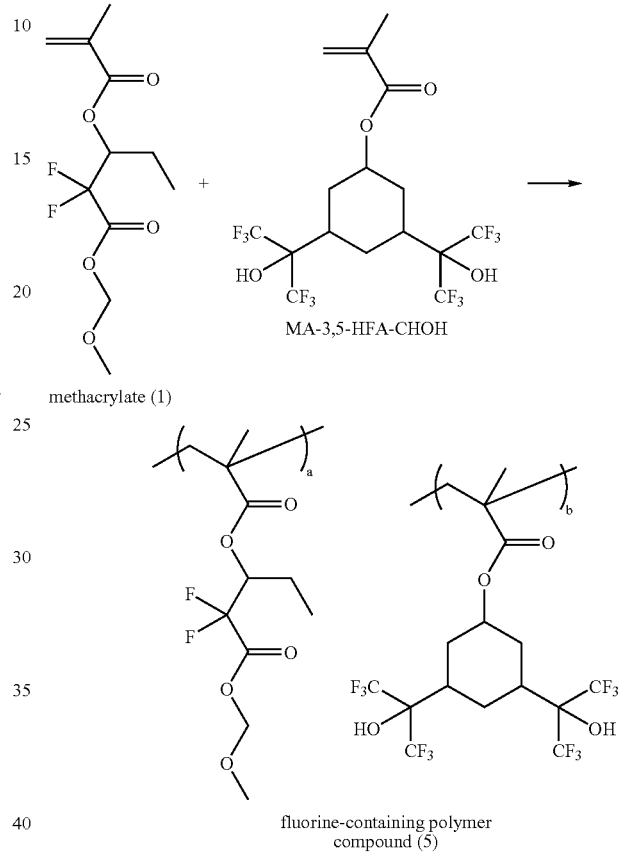

fluorine-containing polymer
compound (5)

Similar to the process of Example 7, a copolymerization was conducted by using two raw materials, methacrylate (1) and MA-3,5-HFA-CHOH, thereby synthesizing fluorine-containing polymer compound (5) in a white solid. The molecular weight was determined by GPC (standard substance: polystyrene). The compositional molar ratio (a/b) of fluorine-containing polymer compound (5) was determined by NMR. The results are shown in Table 1.

TABLE 1

| | Fluorine-containing Polymer Compound | Molecular Weight Mw (Mw/Mn) | Copolymerization Ratio (a/b) |
|---|---|---|---|
| Ex. 7 | (1) | 17,000 (2.41) | — |
| Ex. 8 | (2) | 18,000 (2.25) | 51/49 |
| Ex. 9 | (3) | 17,500 (2.15) | 52/48 |
| Ex. 10 | (4) | 16,800 (1.98) | 49/51 |
| Ex. 11 | (5) | 15,900 (2.02) | 85/15 |

EXAMPLE 12

Fluorine-containing polymer compounds (1), (2), (3), (4) and (5) were each dissolved in propylene glycol methyl acetate, and they were adjusted to have a solid matter content of 14%. Furthermore, triphenylsulfonium triflate (TPS105) made by Midori Kagaku Co., Ltd. as an acid generator was dissolved in a manner to be 5 parts by weight per 100 parts by weight of the polymer compound, thereby preparing resist compositions (R-1, R-2, R-3, R-4 and R-5).

Then, all of the resist compositions were filtered with a membrane filer of a pore diameter of 0.2 μm. Then, each composition was applied to a silicon wafer by spin coating to obtain a resist film of a film thickness of 250 nm. After conducting a preliminary baking at 120° C., an exposure to a 193 nm ultraviolet ray was conducted through a photomask of a 130 nm-size, 1:1 line-and-space (130 nm 1 L/1 S pattern). Then, a post exposure baking was conducted at 120° C. Then, a development was conducted at 22° C. for 1 minute using 2.38 wt % tetramethylammonium hydroxide aqueous solution. As a result, a high-resolution pattern was obtained from each resist composition. There were almost not found inferiority defect in adhesion to substrate, film-forming inferiority defect, development defect, and etching resistance inferiority defect.

The 130 nm 1 L/1 S pattern resolved at the optimum exposure was observed by a critical dimension scanning electron microscope (CD-SEM), S9220 (tradename) of Hitachi High-Technologies Corporation. The results of the evaluation of the patterns, based on that of the resist composition R-1, are shown in Table 2.

TABLE 2

| | Polymer Compound | Pattern Characteristic |
|---|---|---|
| Example 12 Resist Composition | | |
| R-1 | Fluorine-containing Polymer Compound (1) | Slightly Swelled |
| R-2 | Fluorine-containing Polymer Compound (2) | Rectangular |
| R-3 | Fluorine-containing Polymer Compound (3) | Rectangular |
| R-4 | Fluorine-containing Polymer Compound (4) | Rectangular |
| R-5 | Fluorine-containing Polymer Compound (5) | Rectangular |
| Com. Ex. 1 | Polymer Compound (6) | Swelled |
| Com. Ex. 2 | Polymer Compound (7) | Swelled |
| Com. Ex. 3 | Polymer Compound (8) | Swelled |
| Com. Ex. 4 | Polymer Compound (9) | Swelled |

COMPARATIVE EXAMPLE 1

Similar to the process of Example 7, a copolymerization was conducted by using two raw materials, tert-butyl methacrylate and MA-lactone (made by OSAKA ORGANIC CHEMICAL INDUSTRY LTD.), thereby synthesizing polymer compound (6) (see the following formula).

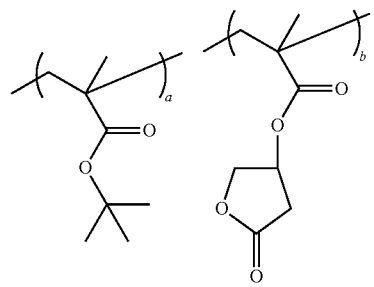

Then, a resist composition and a resist pattern were prepared from polymer compound (6) by the same process as that of Example 12. The result of the evaluation is shown in Table 2.

COMPARATIVE EXAMPLE 2

Similar to the process of Example 7, a copolymerization was conducted by using two raw materials, methyladamantyl methacrylate (MA-MAD, made by DAICEL CHEMICAL INDUSTRIES, LTD.) and hydroxyadamantyl methacrylate (MA-HMA, made by DAICEL CHEMICAL INDUSTRIES, LTD.), thereby synthesizing polymer compound (7) (see the following formula).

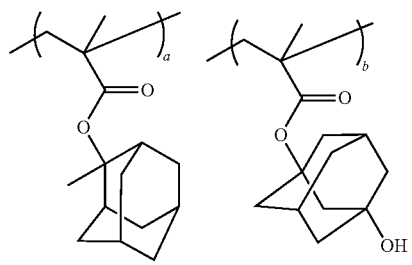

Then, a resist composition and a resist pattern were prepared from polymer compound (7) by the same process as that of Example 12. The result of the evaluation is shown in Table 2.

COMPARATIVE EXAMPLE 3

Similar to the process of Example 7, a copolymerization was conducted by using two raw materials, tert-butyl methacrylate and MA-BTHB-NB, thereby synthesizing polymer compound (8) (see the following formula).

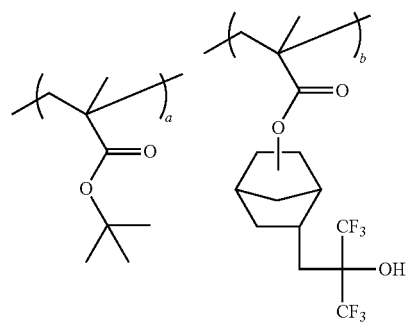

Then, a resist composition and a resist pattern were prepared from polymer compound (8) by the same process as that of Example 12. The result of the evaluation is shown in Table 2.

COMPARATIVE EXAMPLE 4

Similar to the process of Example 7, a copolymerization was conducted by using two raw materials, MA-MAD (made by DAICEL CHEMICAL INDUSTRIES, LTD.) and MA-3, 5-HFA-CHOH, thereby synthesizing polymer compound (9) (see the following formula).

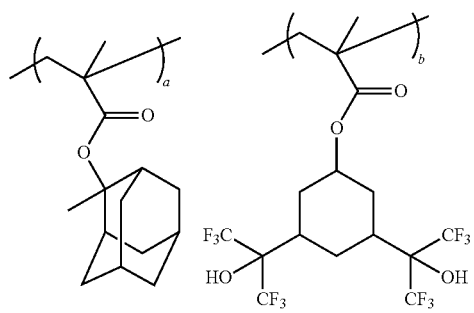

Then, a resist composition and a resist pattern were prepared from polymer compound (9) by the same process as that of Example 12. The result of the evaluation is shown in Table 2.

As is clear from Table 2, the resist compositions R-1 to R-5 according to the present invention provided good results (i.e., rectangular patterns with no or slight swelling, as compared with those of Comparative Examples 1 to 4.

In other words, it is possible to prepare a resist composition that responds to a high-energy ray (e.g., far-ultraviolet ray such as KrF excimer laser (wavelength: 248 nm) or ArF excimer laser (wavelength: 193 nm)) by using a fluorine-containing polymer compound of the present invention. Furthermore, such resist composition is superior in pattern rectangularity as a chemically amplified resist composition by containing an acid-labile protecting group (e.g., acetal group). Therefore, it can extremely preferably be used in the production of integrated circuit devices that are expected in the future to have finer sizes.

What is claimed is:

1. A fluorine-containing polymer compound comprising a repeating unit (a) represented by formula (2),

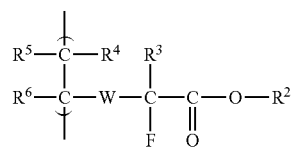

(2)

wherein $R^2$ represents an acid-labile protecting group, $R^3$ represents a fluorine atom or fluorine-containing alkyl group, W represents a bivalent linking group, each of $R^4$, $R^5$ and $R^6$ independently represents a hydrogen atom, fluorine atom or monovalent organic group, and at least two of $R^4$, $R^5$ and $R^6$ may be combined to form a ring, wherein the fluorine-containing polymer compound has a weight-average molecular weight of 1,000 to 1,000,000.

2. A fluorine-containing polymer compound according to claim 1, wherein a partial structure in formula (2), which is represented by formula (9-1),

(9-1)

comprises a structure formed by cleavage of a polymerizable double bond of a group selected from the group consisting of the following groups,

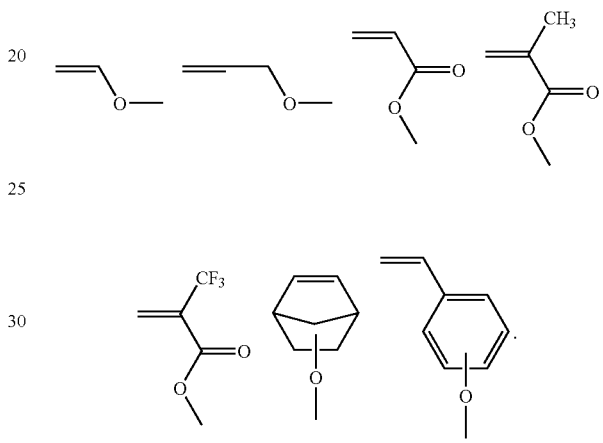

3. A fluorine-containing polymer compound according to claim 1, wherein W represents a bivalent linking group selected from the group consisting of a single bond, —(CR$^7$R$^8$)$_n$— (wherein n represents an integer of 1-10, each of $R^7$ and $R^8$ independently represents a monovalent organic group, and $R^7$ and $R^8$ may be combined to form a ring), —O—, —C(=O)—, —C(=O)O—, —O—C(=O)—, a bivalent alicyclic hydrocarbon group, a bivalent aromatic hydrocarbon group, a thioether group, an ester group, an amide group, a sulfonamide group, a urethane group, a urea group, and combinations of these.

4. A fluorine-containing polymer compound according to claim 1, which comprises a structure formed by cleavage of a polymerizable double bond of a compound selected from the group consisting of the following compounds,

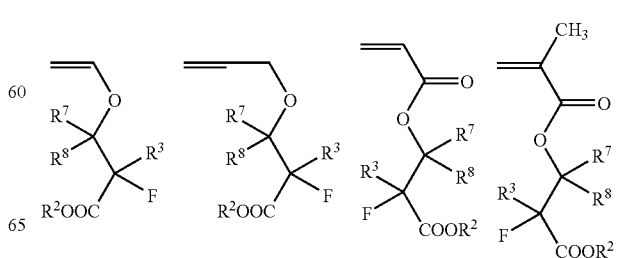

-continued

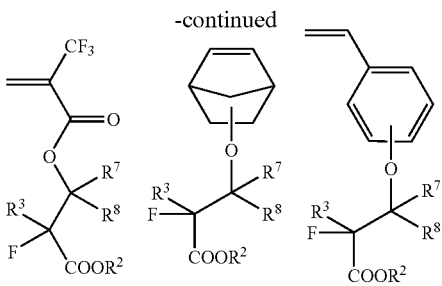

wherein $R^2$ and $R^3$ are defined as in claim 1, $R^7$ represents a hydrogen atom or a straight-chain, branched or cyclic alkyl or fluoroalkyl group, $R^8$ represents a straight-chain, branched or cyclic alkyl or fluoroalkyl group, and $R^7$ and $R^8$ may be combined to form a ring.

5. A fluorine-containing polymer compound according to claim 4, wherein each of $R^7$ and $R^8$ independently represents a $C_1$-$C_4$ straight-chain or branched alkyl or fluoroalkyl group or a $C_3$-$C_{10}$ cyclic alkyl or fluoroalkyl group, or $R^7$ and $R^8$ are bonded together to form a $C_4$-$C_8$ alicyclic hydrocarbon group.

6. A fluorine-containing polymer compound according to claim 4, wherein $R^7$ represents a hydrogen atom or a monovalent organic group selected from the group consisting of methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group,
$R^8$ represents a monovalent organic group selected from the group consisting of methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group, or
$R^7$ and $R^8$ are bonded together to form a cyclopentyl group, cyclohexyl group or cycloheptyl group.

7. A fluorine-containing polymer compound according to claim 6, wherein $R^3$ represents a fluorine atom.

8. A fluorine-containing polymer compound according to claim 1, which comprises a structure formed by cleavage of a polymerizable double bond of one of the following compounds,

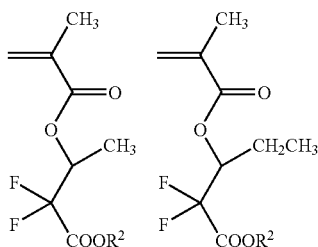

wherein $R^2$ is defined as in claim 1.

9. A fluorine-containing polymer compound according to claim 1, wherein $R^2$ is a monovalent organic group selected from the group consisting of $R^{11}$—O—C(=O)—, $R^{11}$—O—CHR^{12}$—, $CR^{13}R^{14}R^{15}$—, $SiR^{13}R^{14}R^{15}$—, and $R^{11}$—C(=O)—, where $R^{11}$ represents an alkyl group, alicyclic hydrocarbon group, or aryl group; $R^{12}$ represents a hydrogen atom, alkyl group, alicyclic hydrocarbon group, alkenyl group, aralkyl group, alkoxy group, or aryl group; each of $R^{13}$, $R^{14}$ and $R^{15}$ independently represents an alkyl group, alicyclic hydrocarbon group, alkenyl group, aralkyl group, or aryl group; and at least two groups of $R^{13}$, $R^{14}$ and $R^{15}$ may be combined to form a ring.

10. A fluorine-containing polymer compound according to claim 1, further comprising a repeating unit having a side chain with a lactone ring.

11. A fluorine-containing polymer compound according to claim 1, further comprising a repeating unit (b) derived from a polymerizable monomer selected from the group consisting of acrylates, fluorine-containing acrylates, methacrylates, fluorine-containing methacrylates, styrene compounds, fluorine-containing styrene compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds, fluorine-containing norbornene compounds, sulfur dioxide, and vinyl silanes.

12. A fluorine-containing polymer compound according to claim 1, wherein the fluorine-containing polymer compound further comprises a repeating unit (b), and wherein the repeating unit (a) represented by formula (2) and the repeating unit (b) are respectively in 0.1-99.9 mol % and 99.9-0.1 mol %, based on a total mole number of all repeating units contained in the fluorine-containing polymer compound.

13. A resist composition comprising:
a fluorine-containing polymer compound according to claim 1;
an acid generator; and
a solvent.

14. A process for forming a pattern, comprising the steps of:
(a) applying a resist composition according to claim 13 on a substrate to form a resist film;
(b) exposing the resist film to a high-energy ray having a wavelength of 300 nm or shorter or electron beam through a photomask;
(c) heating the exposed resist film; and
(d) developing the heated resist film.

15. A process according to claim 14, further comprising the step of (e) heating the resist film, between the steps (a) and (b).

16. A process according to claim 14, wherein the high-energy ray of step (b) is a $F_2$ excimer laser, ArF excimer laser, KrF excimer laser, or soft X-ray.

17. An electronic device comprising a pattern formed by a process according to claim 14.

* * * * *